(12) United States Patent
Dukesherer et al.

(10) Patent No.: US 7,366,562 B2
(45) Date of Patent: Apr. 29, 2008

(54) METHOD AND APPARATUS FOR SURGICAL NAVIGATION

(75) Inventors: John H. Dukesherer, Lakewood, CO (US); Bruce M. Burg, Louisville, CO (US); Bradley A. Jascob, Superior, CO (US); Paul Kessman, Broomfield, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 430 days.

(21) Appl. No.: 10/688,068

(22) Filed: Oct. 17, 2003

(65) Prior Publication Data

US 2005/0085715 A1   Apr. 21, 2005

(51) Int. Cl.
*A61B 5/05* (2006.01)

(52) U.S. Cl. ...................... 600/424; 606/130
(58) Field of Classification Search ........... 600/424, 600/426, 431, 414, 433
See application file for complete search history.

(56) References Cited

U.S. PATENT DOCUMENTS

| 1,576,781 | A | 3/1926 | Phillips |
|---|---|---|---|
| 1,735,726 | A | 11/1929 | Bornhardt |
| 2,407,845 | A | 9/1946 | Nemeyer |
| 2,650,588 | A | 9/1953 | Drew |
| 2,697,433 | A | 12/1954 | Sehnder |
| 3,016,899 | A | 1/1962 | Stenvall |
| 3,017,887 | A | 1/1962 | Heyer |
| 3,061,936 | A | 11/1962 | Dobbeleer |
| 3,073,310 | A | 1/1963 | Mocarski |
| 3,109,588 | A | 11/1963 | Polhemus et al. |
| 3,294,083 | A | 12/1966 | Alderson |
| 3,367,326 | A | 2/1968 | Frazier |
| 3,439,256 | A | 4/1969 | Kähne et al. |
| 3,577,160 | A | 5/1971 | White |
| 3,614,950 | A | 10/1971 | Rabey |
| 3,644,825 | A | 2/1972 | Davis, Jr. et al. |
| 3,674,014 | A | 7/1972 | Tillander |
| 3,702,935 | A | 11/1972 | Carey et al. |
| 3,704,707 | A | 12/1972 | Halloran |
| 3,821,469 | A | 6/1974 | Whetstone et al. |

(Continued)

FOREIGN PATENT DOCUMENTS

CA            964149            3/1975

(Continued)

OTHER PUBLICATIONS

Adams et al., Computer-Assisted Surgery, IEEE Computer Graphics & Applications, pp. 43-51, (May 1990).

(Continued)

*Primary Examiner*—Brian L. Casler
*Assistant Examiner*—John F Ramirez
(74) *Attorney, Agent, or Firm*—Harness, Dickey & Pierce, P.L.C.

(57) ABSTRACT

A surgical navigation system for navigating a region of a patient includes a non-invasive dynamic reference frame and/or fiducial marker, sensor tipped instruments, and isolator circuits. The dynamic reference frame may be repeatably placed on the patient in a precise location for guiding the instruments. The instruments may be precisely guided by positioning sensors near moveable portions of the instruments. Electrical sources may be electrically isolated from the patient.

26 Claims, 11 Drawing Sheets

U.S. PATENT DOCUMENTS

| | | |
|---|---|---|
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,403,321 A | 9/1983 | DiMarco |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,485,815 A | 12/1984 | Amplatz |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Bludermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |
| 4,701,049 A | 10/1987 | Beckmann et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Öberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |

| | | | | | |
|---|---|---|---|---|---|
| 5,098,426 A | 3/1992 | Sklar et al. | 5,325,873 A | 7/1994 | Hirschi et al. |
| 5,099,845 A | 3/1992 | Besz et al. | 5,329,944 A | 7/1994 | Fabian et al. |
| 5,099,846 A | 3/1992 | Hardy | 5,330,485 A | 7/1994 | Clayman et al. |
| 5,105,829 A | 4/1992 | Fabian et al. | 5,333,168 A | 7/1994 | Fernandes et al. |
| 5,107,839 A | 4/1992 | Houdek et al. | 5,353,795 A | 10/1994 | Souza et al. |
| 5,107,843 A | 4/1992 | Aarnio et al. | 5,353,800 A | 10/1994 | Pohndorf et al. |
| 5,107,862 A | 4/1992 | Fabian et al. | 5,353,807 A | 10/1994 | DeMarco |
| 5,109,194 A | 4/1992 | Cantaloube | 5,359,417 A | 10/1994 | Müller et al. |
| 5,119,817 A | 6/1992 | Allen | 5,368,030 A | 11/1994 | Zinreich et al. |
| 5,142,930 A | 9/1992 | Allen et al. | 5,371,778 A | 12/1994 | Yanof et al. |
| 5,143,076 A | 9/1992 | Hardy et al. | 5,375,596 A | 12/1994 | Twiss et al. |
| 5,152,288 A | 10/1992 | Hoenig et al. | 5,377,678 A | 1/1995 | Dumoulin et al. |
| 5,160,337 A | 11/1992 | Cosman | 5,383,454 A | 1/1995 | Bucholz |
| 5,161,536 A | 11/1992 | Vikomerson et al. | 5,385,146 A | 1/1995 | Goldreyer |
| 5,178,164 A | 1/1993 | Allen | 5,385,148 A | 1/1995 | Lesh et al. |
| 5,178,621 A | 1/1993 | Cook et al. | 5,386,828 A | 2/1995 | Owens et al. |
| 5,186,174 A | 2/1993 | Schlondorff et al. | 5,389,101 A | 2/1995 | Heilbrun et al. |
| 5,187,475 A | 2/1993 | Wagener et al. | 5,391,199 A | 2/1995 | Ben-Haim |
| 5,188,126 A | 2/1993 | Fabian et al. | 5,394,457 A | 2/1995 | Leibinger et al. |
| 5,190,059 A | 3/1993 | Fabian et al. | 5,394,875 A | 3/1995 | Lewis et al. |
| 5,193,106 A | 3/1993 | DeSena | 5,397,329 A | 3/1995 | Allen |
| 5,197,476 A | 3/1993 | Nowacki et al. | 5,398,684 A | 3/1995 | Hardy |
| 5,197,965 A | 3/1993 | Cherry et al. | 5,399,146 A | 3/1995 | Nowacki et al. |
| 5,198,768 A | 3/1993 | Keren | 5,400,384 A | 3/1995 | Fernandes et al. |
| 5,198,877 A | 3/1993 | Schulz | 5,402,801 A | 4/1995 | Taylor |
| 5,207,688 A | 5/1993 | Carol | 5,408,409 A | 4/1995 | Glassman et al. |
| 5,211,164 A | 5/1993 | Allen | 5,413,573 A | 5/1995 | Koivukangas |
| 5,211,165 A | 5/1993 | Dumoulin et al. | 5,417,210 A | 5/1995 | Funda et al. |
| 5,211,176 A | 5/1993 | Ishiguro et al. | 5,419,325 A | 5/1995 | Dumoulin et al. |
| 5,212,720 A | 5/1993 | Landi et al. | 5,423,334 A | 6/1995 | Jordan |
| 5,214,615 A | 5/1993 | Bauer | 5,425,367 A | 6/1995 | Shapiro et al. |
| 5,219,351 A | 6/1993 | Teubner et al. | 5,425,382 A | 6/1995 | Golden et al. |
| 5,222,499 A | 6/1993 | Allen et al. | 5,426,683 A | 6/1995 | O'Farrell, Jr. et al. |
| 5,224,049 A | 6/1993 | Mushabac | 5,426,687 A | 6/1995 | Goodall et al. |
| 5,228,442 A | 7/1993 | Imran | 5,427,097 A | 6/1995 | Depp |
| 5,230,338 A | 7/1993 | Allen et al. | 5,429,132 A | 7/1995 | Guy et al. |
| 5,230,623 A | 7/1993 | Guthrie et al. | 5,433,198 A | 7/1995 | Desai |
| 5,233,990 A | 8/1993 | Barnea | RE35,025 E | 8/1995 | Anderton |
| 5,237,996 A | 8/1993 | Waldman et al. | 5,437,277 A | 8/1995 | Dumoulin et al. |
| 5,249,581 A | 10/1993 | Horbal et al. | 5,443,066 A | 8/1995 | Dumoulin et al. |
| 5,251,127 A | 10/1993 | Raab | 5,443,489 A | 8/1995 | Ben-Haim |
| 5,251,635 A | 10/1993 | Dumoulin et al. | 5,444,756 A | 8/1995 | Pai et al. |
| 5,253,647 A | 10/1993 | Takahashi et al. | 5,445,144 A | 8/1995 | Wodicka et al. |
| 5,255,680 A | 10/1993 | Darrow et al. | 5,445,150 A | 8/1995 | Dumoulin et al. |
| 5,257,636 A | 11/1993 | White | 5,445,166 A | 8/1995 | Taylor |
| 5,257,998 A | 11/1993 | Ota et al. | 5,446,548 A | 8/1995 | Gerig et al. |
| 5,261,404 A | 11/1993 | Mick et al. | 5,447,154 A | 9/1995 | Cinquin et al. |
| 5,265,610 A | 11/1993 | Darrow et al. | 5,448,610 A | 9/1995 | Yamamoto et al. |
| 5,265,611 A | 11/1993 | Hoenig et al. | 5,453,686 A | 9/1995 | Anderson |
| 5,269,759 A | 12/1993 | Hernandez et al. | 5,456,718 A | 10/1995 | Szymaitis |
| 5,271,400 A | 12/1993 | Dumoulin et al. | 5,457,641 A | 10/1995 | Zimmer et al. |
| 5,273,025 A | 12/1993 | Sakiyama et al. | 5,458,718 A | 10/1995 | Venkitachalam |
| 5,274,551 A | 12/1993 | Corby, Jr. | 5,464,446 A | 11/1995 | Dreessen et al. |
| 5,279,309 A | 1/1994 | Taylor et al. | 5,469,847 A | 11/1995 | Zinreich et al. |
| 5,285,787 A | 2/1994 | Machida | 5,478,341 A | 12/1995 | Cook et al. |
| 5,291,199 A | 3/1994 | Overman et al. | 5,478,343 A | 12/1995 | Ritter |
| 5,291,889 A | 3/1994 | Kenet et al. | 5,480,422 A | 1/1996 | Ben-Haim |
| 5,295,483 A | 3/1994 | Nowacki et al. | 5,480,439 A | 1/1996 | Bisek et al. |
| 5,297,549 A | 3/1994 | Beatty et al. | 5,483,961 A | 1/1996 | Kelly et al. |
| 5,299,253 A | 3/1994 | Wessels | 5,485,849 A | 1/1996 | Panescu et al. |
| 5,299,254 A | 3/1994 | Dancer et al. | 5,487,391 A | 1/1996 | Panescu |
| 5,299,288 A | 3/1994 | Glassman et al. | 5,487,729 A | 1/1996 | Avellanet et al. |
| 5,300,080 A | 4/1994 | Clayman et al. | 5,487,757 A | 1/1996 | Truckai et al. |
| 5,305,091 A | 4/1994 | Gelbart et al. | 5,490,196 A | 2/1996 | Rudich et al. |
| 5,305,203 A | 4/1994 | Raab | 5,494,034 A | 2/1996 | Schlondorff et al. |
| 5,306,271 A | 4/1994 | Zinreich et al. | 5,503,416 A | 4/1996 | Aoki et al. |
| 5,307,072 A | 4/1994 | Jones, Jr. | 5,513,637 A | 5/1996 | Twiss et al. |
| 5,309,913 A | 5/1994 | Kormos et al. | 5,514,146 A | 5/1996 | Lam et al. |
| 5,315,630 A | 5/1994 | Sturm et al. | 5,515,160 A | 5/1996 | Schulz et al. |
| 5,316,024 A | 5/1994 | Hirschi et al. | 5,517,990 A | 5/1996 | Kalfas et al. |
| 5,318,025 A | 6/1994 | Dumoulin et al. | 5,531,227 A | 7/1996 | Schneider |
| 5,320,111 A | 6/1994 | Livingston | 5,531,520 A | 7/1996 | Grimson et al. |
| 5,325,728 A | 7/1994 | Zimmerman et al. | 5,542,938 A | 8/1996 | Avellanet et al. |

| | | | | | | |
|---|---|---|---|---|---|---|
| 5,543,951 A | 8/1996 | Moehrmann | | 5,752,513 A | 5/1998 | Acker et al. |
| 5,546,940 A | 8/1996 | Panescu et al. | | 5,755,725 A | 5/1998 | Druais |
| 5,546,949 A | 8/1996 | Frazin et al. | | RE35,816 E | 6/1998 | Schulz |
| 5,546,951 A | 8/1996 | Ben-Haim | | 5,758,667 A | 6/1998 | Slettenmark |
| 5,551,429 A | 9/1996 | Fitzpatrick et al. | | 5,762,064 A | 6/1998 | Polyani |
| 5,558,091 A | 9/1996 | Acker et al. | | 5,767,669 A | 6/1998 | Hansen et al. |
| 5,566,681 A | 10/1996 | Manwaring et al. | | 5,767,699 A | 6/1998 | Hansen et al. |
| 5,568,384 A | 10/1996 | Robb et al. | | 5,767,960 A | 6/1998 | Orman |
| 5,568,809 A | 10/1996 | Ben-haim | | 5,769,789 A | 6/1998 | Wang et al. |
| 5,572,999 A | 11/1996 | Funda et al. | | 5,769,843 A | 6/1998 | Abela et al. |
| 5,573,533 A | 11/1996 | Strul | | 5,769,861 A | 6/1998 | Vilsmeier |
| 5,575,794 A | 11/1996 | Walus et al. | | 5,772,594 A | 6/1998 | Barrick |
| 5,575,798 A | 11/1996 | Koutrouvelis | | 5,775,322 A | 7/1998 | Silverstein et al. |
| 5,583,909 A | 12/1996 | Hanover | | 5,776,064 A | 7/1998 | Kalfas et al. |
| 5,588,430 A | 12/1996 | Bova et al. | | 5,782,765 A | 7/1998 | Jonkman |
| 5,590,215 A | 12/1996 | Allen | | 5,787,886 A | 8/1998 | Kelly et al. |
| 5,592,939 A | 1/1997 | Martinelli | | 5,792,055 A | 8/1998 | McKinnon |
| 5,595,193 A | 1/1997 | Walus et al. | | 5,795,294 A | 8/1998 | Luber et al. |
| 5,596,228 A | 1/1997 | Anderton et al. | | 5,797,849 A | 8/1998 | Vesely et al. |
| 5,600,330 A | 2/1997 | Blood | | 5,799,055 A | 8/1998 | Peshkin et al. |
| 5,603,318 A | 2/1997 | Heilbrun et al. | | 5,799,099 A | 8/1998 | Wang et al. |
| 5,611,025 A | 3/1997 | Lorensen et al. | | 5,800,352 A * | 9/1998 | Ferre et al. .................. 600/407 |
| 5,617,462 A | 4/1997 | Spratt | | 5,800,535 A | 9/1998 | Howard, III |
| 5,617,857 A | 4/1997 | Chader et al. | | 5,802,719 A | 9/1998 | O'Farrell, Jr. et al. |
| 5,619,261 A | 4/1997 | Anderton | | 5,803,089 A | 9/1998 | Ferre et al. |
| 5,622,169 A | 4/1997 | Golden et al. | | 5,807,252 A | 9/1998 | Hassfeld et al. |
| 5,622,170 A | 4/1997 | Schulz | | 5,810,008 A | 9/1998 | Dekel et al. |
| 5,627,873 A | 5/1997 | Hanover et al. | | 5,810,728 A | 9/1998 | Kuhn |
| 5,628,315 A | 5/1997 | Vilsmeier et al. | | 5,810,735 A | 9/1998 | Halperin et al. |
| 5,630,431 A | 5/1997 | Taylor | | 5,820,553 A | 10/1998 | Hughes |
| 5,636,644 A | 6/1997 | Hart et al. | | 5,823,192 A | 10/1998 | Kalend et al. |
| 5,638,819 A | 6/1997 | Manwaring et al. | | 5,823,958 A | 10/1998 | Truppe |
| 5,640,170 A | 6/1997 | Anderson | | 5,828,725 A | 10/1998 | Levinson |
| 5,642,395 A | 6/1997 | Anderton et al. | | 5,828,770 A | 10/1998 | Leis et al. |
| 5,643,268 A | 7/1997 | Vilsmeier et al. | | 5,829,444 A | 11/1998 | Ferre et al. |
| 5,645,065 A | 7/1997 | Shapiro et al. | | 5,831,260 A | 11/1998 | Hansen |
| 5,646,524 A | 7/1997 | Gilboa | | 5,833,608 A | 11/1998 | Acker |
| 5,647,361 A | 7/1997 | Damadian | | 5,834,759 A | 11/1998 | Glossop |
| 5,662,111 A | 9/1997 | Cosman | | 5,836,954 A | 11/1998 | Heilbrun et al. |
| 5,664,001 A | 9/1997 | Tachibana et al. | | 5,840,024 A | 11/1998 | Taniguchi et al. |
| 5,674,296 A | 10/1997 | Bryan et al. | | 5,840,025 A | 11/1998 | Ben-Haim |
| 5,676,673 A | 10/1997 | Ferre et al. | | 5,843,076 A | 12/1998 | Webster, Jr. et al. |
| 5,681,260 A | 10/1997 | Ueda et al. | | 5,848,967 A | 12/1998 | Cosman |
| 5,682,886 A | 11/1997 | Delp et al. | | 5,851,183 A | 12/1998 | Bucholz |
| 5,682,890 A | 11/1997 | Kormos et al. | | 5,865,846 A | 2/1999 | Bryan et al. |
| 5,690,108 A | 11/1997 | Chakeres | | 5,868,674 A | 2/1999 | Glowinski et al. |
| 5,694,945 A | 12/1997 | Ben-Haim | | 5,868,675 A | 2/1999 | Henrion et al. |
| 5,695,500 A | 12/1997 | Taylor et al. | | 5,871,445 A | 2/1999 | Bucholz |
| 5,695,501 A | 12/1997 | Carol et al. | | 5,871,455 A | 2/1999 | Ueno |
| 5,696,500 A | 12/1997 | Taylor et al. | | 5,871,487 A | 2/1999 | Warner et al. |
| 5,697,377 A | 12/1997 | Wittkampf | | 5,873,822 A | 2/1999 | Ferre et al. |
| 5,702,406 A | 12/1997 | Vilsmeier et al. | | 5,882,304 A | 3/1999 | Ehnholm et al. |
| 5,711,299 A | 1/1998 | Manwaring et al. | | 5,884,410 A | 3/1999 | Prinz |
| 5,713,946 A | 2/1998 | Ben-Haim | | 5,889,834 A | 3/1999 | Vilsmeier et al. |
| 5,715,822 A | 2/1998 | Watkins | | 5,891,034 A | 4/1999 | Bucholz |
| 5,715,836 A | 2/1998 | Kliegis et al. | | 5,891,157 A | 4/1999 | Day et al. |
| 5,718,241 A | 2/1998 | Ben-Haim et al. | | 5,904,691 A | 5/1999 | Barnett et al. |
| 5,727,552 A | 3/1998 | Ryan | | 5,907,395 A | 5/1999 | Schultz et al. |
| 5,727,553 A | 3/1998 | Saad | | 5,913,820 A | 6/1999 | Bladen et al. |
| 5,729,129 A | 3/1998 | Acker | | 5,920,395 A | 7/1999 | Schulz |
| 5,730,129 A | 3/1998 | Darrow et al. | | 5,921,992 A | 7/1999 | Costales et al. |
| 5,730,130 A | 3/1998 | Fitzpatrick et al. | | 5,923,727 A | 7/1999 | Navab |
| 5,732,703 A | 3/1998 | Kalfas et al. | | 5,928,248 A | 7/1999 | Acker |
| 5,735,278 A | 4/1998 | Hoult et al. | | 5,938,603 A | 8/1999 | Ponzi |
| 5,738,096 A | 4/1998 | Ben-Haim | | 5,938,694 A | 8/1999 | Jaraczewski et al. |
| 5,740,802 A | 4/1998 | Nafis et al. | | 5,947,980 A | 9/1999 | Jensen et al. |
| 5,740,808 A | 4/1998 | Panescu et al. | | 5,947,981 A | 9/1999 | Cosman |
| 5,741,214 A | 4/1998 | Ouchi et al. | | 5,950,629 A | 9/1999 | Taylor et al. |
| 5,742,394 A | 4/1998 | Hansen | | 5,951,571 A | 9/1999 | Audette |
| 5,744,953 A | 4/1998 | Hansen | | 5,954,647 A | 9/1999 | Bova et al. |
| 5,748,767 A | 5/1998 | Raab | | 5,957,844 A | 9/1999 | Dekel et al. |
| 5,749,362 A | 5/1998 | Funda et al. | | 5,964,796 A | 10/1999 | Imran |
| 5,749,835 A | 5/1998 | Glantz | | 5,967,980 A | 10/1999 | Ferre et al. |

| | | |
|---|---|---|
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,024,695 A | 2/2000 | Greenberg et al. |
| 6,050,724 A | 4/2000 | Schmitz et al. |
| 6,059,718 A | 5/2000 | Taniguchi et al. |
| 6,063,022 A | 5/2000 | Ben-Haim |
| 6,071,288 A | 6/2000 | Carol et al. |
| 6,073,043 A | 6/2000 | Schneider |
| 6,076,008 A | 6/2000 | Bucholz |
| 6,096,050 A | 8/2000 | Audette |
| 6,104,944 A | 8/2000 | Martinelli |
| 6,106,464 A | 8/2000 | Bass et al. |
| 6,118,845 A | 9/2000 | Simon et al. |
| 6,122,538 A | 9/2000 | Sliwa, Jr. et al. |
| 6,122,541 A | 9/2000 | Cosman et al. |
| 6,131,396 A | 10/2000 | Duerr et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,194,639 B1 | 2/2001 | Botella et al. |
| 6,201,387 B1 | 3/2001 | Govari |
| 6,203,497 B1 | 3/2001 | Dekel et al. |
| 6,211,666 B1 | 4/2001 | Acker |
| 6,223,067 B1 | 4/2001 | Vilsmeier |
| 6,233,476 B1 | 5/2001 | Strommer et al. |
| 6,246,231 B1 | 6/2001 | Ashe |
| 6,253,770 B1 | 7/2001 | Acker et al. |
| 6,259,942 B1 | 7/2001 | Westermann et al. |
| 6,273,896 B1 | 8/2001 | Franck et al. |
| 6,285,902 B1 | 9/2001 | Kienzle, III et al. |
| 6,298,262 B1 | 10/2001 | Franck et al. |
| 6,314,310 B1 | 11/2001 | Ben-Haim et al. |
| 6,332,089 B1 | 12/2001 | Acker et al. |
| 6,341,231 B1 | 1/2002 | Ferre et al. |
| 6,351,659 B1 | 2/2002 | Vilsmeier |
| 6,370,411 B1 | 4/2002 | Osadchy et al. |
| 6,381,485 B1 | 4/2002 | Hunter et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,445,943 B1 | 9/2002 | Ferre et al. |
| 6,447,488 B2 | 9/2002 | Ishikawa et al. |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,490,475 B1 | 12/2002 | Seeley et al. |
| 6,493,573 B1 | 12/2002 | Martinelli et al. |
| 6,498,944 B1 | 12/2002 | Ben-Haim et al. |
| 6,499,488 B1 | 12/2002 | Hunter et al. |
| 6,516,046 B1 | 2/2003 | Fröhlich et al. |
| 6,527,443 B1 | 3/2003 | Vilsmeier et al. |
| 6,551,325 B2 | 4/2003 | Neubauer et al. |
| 6,584,174 B2 | 6/2003 | Schubert et al. |
| 6,609,022 B2 | 8/2003 | Vilsmeier et al. |
| 6,611,700 B1 | 8/2003 | Vilsmeier et al. |
| 6,640,128 B2 | 10/2003 | Vilsmeier et al. |
| 6,694,162 B2 | 2/2004 | Hartlep |
| 6,701,179 B1 | 3/2004 | Martinelli et al. |
| 2001/0007918 A1 | 7/2001 | Vilsmeier et al. |
| 2001/0044578 A1 | 11/2001 | Ben-Haim et al. |
| 2002/0087101 A1* | 7/2002 | Barrick et al. ............... 600/587 |
| 2002/0095081 A1 | 7/2002 | Vilsmeier |
| 2003/0009169 A1 | 1/2003 | Young et al. |
| 2003/0097061 A1 | 5/2003 | Ferre et al. |
| 2004/0024309 A1 | 2/2004 | Ferre et al. |
| 2004/0097805 A1 | 5/2004 | Verard et al. |

FOREIGN PATENT DOCUMENTS

| | | |
|---|---|---|
| DE | 3042343 A1 | 6/1982 |
| DE | 35 08730 | 3/1985 |
| DE | 37 17 871 | 5/1987 |
| DE | 38 38011 | 11/1988 |
| DE | 3831278 A1 | 3/1989 |
| DE | 42 13 426 | 4/1992 |
| DE | 42 25 112 | 7/1992 |
| DE | 4233978 C1 | 4/1994 |
| DE | 197 15 202 | 4/1997 |
| DE | 197 47 427 | 10/1997 |
| DE | 197 51 761 | 11/1997 |
| DE | 196 31 303 | 2/1998 |
| DE | 198 32 296 | 7/1998 |
| DE | 10085137 | 10/1999 |
| DE | 10335388 | 2/2005 |
| EP | 0 062 941 | 3/1982 |
| EP | 0 119 660 | 9/1984 |
| EP | 0 155 857 | 1/1985 |
| EP | 0 319 844 A1 | 1/1988 |
| EP | 0 326 768 | 12/1988 |
| EP | 0419729 A1 | 9/1989 |
| EP | 0350996 A1 | 1/1990 |
| EP | 0 651 968 A1 | 8/1990 |
| EP | 0 427 358 | 10/1990 |
| EP | 0 456 103 | 5/1991 |
| EP | 0 581 704 B1 | 7/1993 |
| EP | 0655138 B1 | 8/1993 |
| EP | 0894473 A2 | 1/1995 |
| EP | 0 908 146 | 10/1998 |
| EP | 0 930 046 | 10/1998 |
| EP | 1523951 | 4/2005 |
| FR | 2417970 | 2/1979 |
| FR | 2 618 211 | 7/1987 |
| GB | 2 094 590 | 2/1982 |
| GB | 2 164 856 | 10/1984 |
| JP | 61-94639 | 10/1984 |
| JP | 62-327 | 6/1985 |
| JP | 63-240851 | 3/1987 |
| JP | 3-267054 | 3/1990 |
| JP | 2765738 | 10/1998 |
| WO | WO 88/09151 | 12/1988 |
| WO | WO 89/05123 | 6/1989 |
| WO | WO 90/05494 | 11/1989 |
| WO | WO 91/03982 | 4/1991 |
| WO | WO 91/04711 | 4/1991 |
| WO | WO 91/07726 | 5/1991 |
| WO | WO 92/03090 | 3/1992 |
| WO | WO 92/06645 | 4/1992 |
| WO | WO 94/04938 | 3/1994 |
| WO | WO 95/07055 | 9/1994 |
| WO | WO 94/23647 | 10/1994 |
| WO | WO 94/24933 | 11/1994 |
| WO | WO 96/32059 | 11/1995 |

| | | |
|---|---|---|
| WO | WO 96/11624 | 4/1996 |
| WO | WO96/32060 | 10/1996 |
| WO | WO 97/49453 | 6/1997 |
| WO | WO 97/36192 | 10/1997 |
| WO | WO 99/23956 | 11/1997 |
| WO | WO 98/08554 | 3/1998 |
| WO | WO 98/38908 | 9/1998 |
| WO | WO 99/15097 | 9/1998 |
| WO | WO 99/21498 | 10/1998 |
| WO | WO 99/27839 | 12/1998 |
| WO | WO 99/33406 | 12/1998 |
| WO | WO 99/38449 | 1/1999 |
| WO | WO 99/52094 | 4/1999 |
| WO | WO 99/26549 | 6/1999 |
| WO | WO 99/29253 | 6/1999 |
| WO | WO 99/37208 | 7/1999 |
| WO | WO 99/60939 | 12/1999 |
| WO | WO 01/30437 A1 | 5/2001 |
| WO | WO-0130257 | 5/2001 |

OTHER PUBLICATIONS

Bergstrom et al. Stereotaxic Computed Tomography, Am. J. Roentgenol, vol. 127 pp. 167-170 (1976).

Brown, R., M.D., A Stereotactic Head Frame for Use with CT Body Scanners, Investigative Radiology © J.B. Lippincott Company, pp. 300-304 (Jul.-Aug. 1979).

Bucholz, R.D., et al. Image-guided surgical techniques for infections and trauma of the central nervous system, Neurosurg. Clinics of N.A., vol. 7, No. 2, pp. 187-200 (1996).

Bucholz, R.D., et al., A Comparison of Sonic Digitizers Versus Light Emitting Diode-Based Localization, Interactive Image-Guided Neurosurgery, Chapter 16, pp. 179-200 (1993).

Bucholz, R.D., et al., Intraoperative localization using a three dimensional optical digitizer, SPIE—The Intl. Soc. for Opt. Eng., vol. 1894, pp. 312-322 (Jan. 17-19, 1993).

Bucholz, R.D., et al., Intraoperative Ultrasonic Brain Shift Monitor and Analysis, Stealth Station Marketing Brochure (2 pages), undated.

Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics and Computer-Assisted Surgery, Grenoble, France, pp. 459-466 (Mar. 19-22, 1997).

Cutting M.D. et al., Optical Tracking of Bone Fragments During Craniofacial Surgery, Second Annual International Symposium on Medical Robotics and Computer Assisted Surgery, pp. 221-225, (Nov. 1995).

Friets, E.M., et al. A Frameless Stereotaxic Operating Microscope for Neurosurgery, IEEE Trans. on Biomed. Eng., vol. 36, No. 6, pp. 608-617 (Jul. 1989).

Gallen, C.C., et al., Intracranial Neurosurgery Guided by Functional Imaging, Surg. Neurol., vol. 42, pp. 523-530 (1994).

Galloway, R.L., Jr. et al, Optical localization for interactive, image-guided neurosurgery, SPIE, vol. 2164, pp. 137-145, undated.

Galloway, R.L., et al., Interactive Image-Guided Neurosurgery, IEEE Trans. on Biomed. Eng., vol. 89, No. 12, pp. 1226-1231 (1992).

Gomez, C.R., et al., Transcranial Doppler Ultrasound Following Closed Head Injury: Vasospasm or Vasoparalysis?, Surg. Neurol., vol. 35, pp. 30-35 (1991).

Grimson, W.E.L., An Automatic Registration Method for Frameless Stereotaxy, Image Guided Surgery, and enhanced Reality Visualization, IEEE, pp. 430-436 (1994).

Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6, pp. 62-69 (Jun. 1999).

Guthrie, B.L., Graphic-Interactive Cranial Surgery: The Operating Arm System, Handbook of Stereotaxy Using the CRW Apparatus, Chapter 13, pp. 193-211, undated.

Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).

Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).

Heilbrun, M.P., Computer Tomography—Guided Stereotactic Systems, Clinical Neurosurgery, Chapter 31, pp. 564-581 (1983).

Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).

Kall, B., The Impact of Computer and Imgaging Technology on Stereotactic Surgery, Proceedings of the Meeting of the American Society for Stereotactic and Functional Neurosurgery, pp. 10-22 (1987).

Kato, A., et al., A frameless, armless navigational system for computer-assisted neurosurgery, J. Neurosurg., vol. 74, pp. 845-849 (May 1991).

Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).

Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).

Kelly, P.J., Computer-Directed Stereotactic Resection of Brain Tumors, Neurologica Operative Atlas, vol. 1, No. 4, pp. 299-313 (1991).

Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).

Kim, W.S. et al., A Helmet Mounted Display for Telerobotics, IEEE, pp. 543-547 (1988).

Klimek, L., et al., Long-Term Experience with Different Types of Localization Systems in Skull-Base Surgery, Ear, Nose & Throat Surgery, Chapter 51, pp. 635-638, undated.

Kosugi, Y., et al., An Articulated Neurosurgical Navigation System Using MRI and CT Images, IEEE Trans. on Biomed, Eng. vol. 35, No. 2, pp. 147-152 (Feb. 1988).

Krybus, W., et al., Navigation Support for Surgery by Means of Optical Position Detection, Computer Assisted Radiology Proceed. of the Intl. Symp. CAR '91 Computed Assisted Radiology, pp. 362-366 (Jul. 3-6, 1991).

Kwoh, Y.S., Ph.D., et al., A New Computerized Tomographic-Aided Robotic Stereotaxis System, Robotics Age, vol. 7, No. 6, pp. 17-22 (Jun. 1985).

Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).

Lavallee, S., et al., Computer Assisted Medical Interventions, NATO ASI Series, vol. F 60, 3d Imaging in Medic., pp. 301-312 (1990).

Leavitt, D.D., et al., Dynamic Field Shaping to Optimize Stereotactic Radiosurgery, I.J. Rad. Onc. Biol. Physc., vol. 21, pp. 1247-1255 (1991).

Maurer, Jr., et al, Registration of Head CT Images to Physical Space Using a Weighted Combination of Points and Surfaces, IEEE Trans. on Med. Imaging, vol. 17, No. 5, pp. 753-761 (Oct. 1998).

McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).

Ng, W.S. et al., Robotic Surgery—A First-Hand Experience in Transurethral Resection of the Prostate Surgery, IEEE Eng. in Med. and Biology, pp. 120-125 (Mar. 1993).

Penn, R.D., et al., Stereotactic Surgery with Image Processing of Computerized Tomographic Scans, Neurosurgery, vol. 3, No. 2, pp. 157-163 (Sep.-Oct. 1978).

Pixsys, 3-D Digitizing Accessories, by Pixsys (marketing brochure)(undated) (2 pages).

Reinhardt, H., et al., A Computer-Assisted Device for Intraoperative CT-Correlated Localization of Brain Tumors, pp. 51-58 (1988).

Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).

Reinhardt, H.F., et al., Mikrochirugische Entfernung tiefliegender Gefäßmißbildungen mit Hilfe der Sonar-Stereometrie (Microsurgical Removal of Deep-Seated Vascular Malformations Using Sonar Stereometry). Ultraschall in Med. 12, pp. 80-83 (1991).

Reinhardt, Hans. F., Neuronavigation: A Ten-Year Review, Neurosurgery, pp. 329-341, undated.

Simon, D.A., Accuracy Validation in Image-Guided Orthopaedic Surgery, Second Annual Intl. Symp. on Med. Rob. an Comp-Assisted surgery, MRCAS '95, pp. 185-192, undated.

Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).

Tan, K., Ph.D., et al., A frameless stereotactic approach to neurosurgical planning based on retrospective patient-image registration, J Neurosurgy, vol. 79, pp. 296-303 (Aug. 1993).

Thompson, et al., A System for Anatomical and Functional Mapping of the Human Thalamus, Computers and Biomedical Research, vol. 10, pp. 9-24 (1977).

Trobraugh, J.W., et al., Frameless Stereotactic Ultrasonography: Method and Applications, Computerized Medical Imaging and Graphics, vol. 18, No. 4, pp. 235-246 (1994).

Von Hanwhr et al., Foreword, Computerized Medical Imaging and Graphics, vol. 18, No. 4, pp. 225-228, (Jul.-Aug. 1994).

Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.

Benzel et al., "Magnetic Source Imaging: a Review of the Magnes System of Biomagnetic Technologies Incorporated," Neurosurgery, vol. 33, No. 2 (Aug. 1993), pp. 252-259.

Bouazza-Marouf et al.; "Robotic-Assisted Internal Fixation of Femoral Fractures", IMECHE., pp. 51-58 (1995).

Brack et al., "Accurate X-ray Based Navigation in Computer-Assisted Orthopedic Surgery," CAR '98, pp. 716-722.

Bryan, "Bryan Cervical Disc System Single Level Surgical Technique", Spinal Dynamics, 2002, pp. 1-33.

Bucholz et al., "Variables affecting the accuracy of stereotactic localizationusing computerized tomography," Journal of Neurosurgery, vol. 79, Nov. 1993, pp. 667-673.

Champleboux, "Utilisation de Fonctions Splines pour la Mise au Point D'un Capteur Tridimensionnal sans Contact," Quelques Applications Medicales, Jul. 1991.

Cinquin et al., "Computer Assisted Medical Interventions," IEEE Engineering in Medicine and Biology, May/Jun. 1995, pp. 254-263.

Cinquin et al., "Computer Assisted Medical Interventions," International Advanced Robotics Programme, Sep. 1989, pp. 63-65.

Clarysse et al., "A Computer-Assisted System for 3-D Frameless Localization in Stereotaxic MRI," IEEE Transactions on Medical Imaging, vol. 10, No. 4, Dec. 1991, pp. 523-529.

Feldmar et al., "3D-2D Projective Registration of Free-Form Curves and Surfaces," Rapport de recherche (Inria Sophia Antipolis), 1994, pp. 1-44.

Foley et al., "Fundamentals of Interactive Computer Graphics," The Systems Programming Series, Chapter 7, Jul. 1984, pp. 245-266.

Foley et al., "Image-guided Intraoperative Spinal Localization," Intraoperative Neuroprotection, Chapter 19, 1996, pp. 325-340.

Foley, "The StealthStation: Three-Dimensional Image-Interactive Guidance for the Spine Surgeon," Spinal Frontiers, Apr. 1996, pp. 7-9.

Leksell et al., "Stereotaxis and Tomography—A Technical Note," ACTA Neurochirurgica, vol. 52, 1980, pp. 1-7.

Lemieux et al., "A Patient-to-Computed-Tomography Image Registration Method Based on Digitally Reconstructed Radiographs," Med. Phys. 21 (11), Nov. 1994, pp. 1749-1760.

Levin et al., "The Brain: Integrated Three-dimensional Display of MR and PET Images," Radiology, vol. 172, No. 3, Sep. 1989, pp. 783-789.

Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.

Mazier et al., Chirurgie de la Colonne Vertebrale Assistee par Ordinateur: Appication au Vissage Pediculaire, Innov. Tech. Biol. Med., vol. 11, No. 5, 1990, pp. 559-566.

Pelizzari et al., "Accurate Three-Dimensional Registration of CT, PET, and/or MR Images of the Brain," Journal of Computer Assisted Tomography, Jan./Feb. 1989, pp. 20-26.

Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).

Pelizzari et al., No. 528—"Three Dimensional Correlation of PET, CT and MRI Images," The Journal of Nuclear Medicine, vol. 28, No. 4, Apr. 1987, p. 682.

Phillips et al., "Image Guided Orthopaedic Surgery Design and Analysis," Trans Inst. MC, vol. 17, No. 5, 1995, pp. 251-264.

Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.

Reinhardt et al., "CT-Guided 'Real Time' Stereotaxy," ACTA Neurochirurgica, 1989.

Roberts et al., "A frameless stereotaxic integration of computerized tomographic imaging and the operating microscope," J. Neurosurg., vol. 65, Oct. 1986, pp. 545-549.

Rosenbaum et al., "Computerized Tomography Guided Stereotaxis: A New Approach," Applied Neurophysiology, vol. 43, No. 3-5, 1980, pp. 172-173.

Sautot, "Vissage Pediculaire Assiste Par Ordinateur," Sep. 20, 1994.

Hamadeh et al., "Towards Automatic Registration Between CT and X-ray Images: Cooperation Between 3D/2D Registration and 2D Edge Detection," MRCAS '95, pp. 39-46.

Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.

Shelden et al., "Development of a computerized microsteroetaxic method for localization and removal of minute CNS lesions under direct 3-D vision," J. Neurosurg., vol. 52, 1980, pp. 21-27.

Smith et al., "Computer Methods for Improved Diagnostic Image Display Applied to Stereotactic Neurosurgery," Automedical, vol. 14, 1992, pp. 371-382 (4 unnumbered pages).

Smith et al., "The Neurostation™—A Highly Accurate, Minimally Invasive Solution to Frameless Stereotactic Neurosurgery," Computerized Medical Imaging and Graphics, vol. 18, Jul.-Aug. 1994, pp. 247-256.

The Laitinen Stereotactic System, E2-E6, undated.

Viant et al., "A Computer Assisted Orthopaedic System for Distal Locking of Intramedullary Nails," Proc. of MediMEC '95, Bristol, 1995, pp. 86-91.

Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.

Watanabe, "Neuronavigator," Igaku-no-Ayumi, vol. 137, No. 6, May 10, 1986, pp. 1-4.

Weese et al., "An Approach to 2D/3D Registration of a Vertebra in 2D X-ray Fluoroscopies with 3D CT Images," pp. 119-128, undated.

Germano, "Instrumentation, Technique and Technology", Neurosurgery, vol. 37, No. 2, Aug. 1995, pp. 348-350.

Merloz, et al., "Computer Assisted Spine Surgery", Clinical Assisted Spine Surgery, No. 337, pp. 86-96, undated.

Hatch, et al., "Reference-Display System for the Integration of CT Scanning and the Operating Microscope", Proceedings of the Eleventh Annual Northeast Bioengineering Conference, Mar. 14-15, 1985, pp. 252-254.

Champleboux et al., "Accurate Calibration of Cameras and Range Imaging Sensors: the NPBS Method," IEEE International Conference on Robotics and Automation, Nice, France, May 1992.

"Prestige Cervical Disc System Surgical Technique", 12 pgs., undated.

Adams et al., "Orientation Aid for Head and Neck Surgeons," Innov. Tech. Biol. Med., vol. 13, No. 4, 1992, pp. 409-424.

Barrick et al., "Prophylactic Intramedullary Fixation of the Tibia for Stress Fracture in a Professional Athlete," Journal of Orthopaedic Trauma, vol. 6, No. 2, pp. 241-244 (1992).

Barrick et al., "Technical Difficulties with the Brooker-Wills Nail in Acute Fractures of the Femur," Journal of Orthopaedic Trauma, vol. 6, No. 2, pp. 144-150 (1990).

Barrick, "Distal Locking Screw Insertion Using a Cannulated Drill Bit: Technical Note," Journal of Orthopaedic Trauma, vol. 7, No. 3, 1993, pp. 248-251.

Jacques et al., "Computerized three-dimensional stereotaxic removal of small central nervous system lesion in patients," J. Neurosurg., vol. 53, Dec. 1980, pp. 816-820.

Joskowicz et al., "Computer-Aided Image-Guided Bone Fracture Surgery: Concept and Implementation," CAR '98, pp. 710-715.

Kelly et al., "Computer-assisted stereotaxic laser resection of intra-axial brain neoplasms," Journal of Neurosurgery, vol. 64, Mar. 1986, pp. 427-439.

Kelly et al., "Precision Resection of Intra-Axial CNS Lesions by CT-Based Stereotactic Craniotomy and Computer Monitored CO2 Laser," Acta Neurochirurgica, vol. 68, 1983, pp. 1-9.

Laitinen et al., "An Adapter for Computed Tomography-Guided, Stereotaxis," Surg. Neurol., 1985, pp. 559-566.

Laitinen, "Noninvasive multipurpose stereoadapter," Neurological Research, Jun. 1987, pp. 137-141.

Lavallee et al, "Matching 3-D Smooth Surfaces with their 2-D Projections using 3-D Distance Maps," SPIE, vol. 1570, Geometric Methods in Computer Vision, 1991, pp. 322-336.

Lavallee et al., "Computer Assisted Driving of a Needle into the Brain," Proceedings of the International Symposium CAR '89, Computer Assisted Radiology, 1989, pp. 416-420.

Lavallee et al., "Computer Assisted Interventionist Imaging: The Instance of Stereotactic Brain Surgery," North-Holland MEDINFO 89, Part 1, 1989, pp. 613-617.

Lavallee et al., "Computer Assisted Spine Surgery: A Technique For Accurate Transpedicular Screw Fixation Using CT Data and a 3-D Optical Localizer," TIMC, Faculte de Medecine de Grenoble, undated.

Lavallee et al., "Image guided operating robot: a clinical application in stereotactic neurosurgery," Proceedings of the 1992 IEEE Internation Conference on Robotics and Automation, May 1992, pp. 618-624.

Lavallee et al., "Matching of Medical Images for Computed and Robot Assisted Surgery," IEEE EMBS, Orlando, 1991.

Lavallee, "A New System for Computer Assisted Neurosurgery," IEEE Engineering in Medicine & Biology Society 11th Annual International Conference, 1989, pp. 0926-0927.

Lavallee, "VI Adaption de la Methodologie a Quelques Applications Cliniques," Chapitre VI, pp. 133-148, undated.

Gildenberg et al., "Calculation of Stereotactic Coordinates from the Computed Tomographic Scan," Neurosurgery, vol. 10, No. 5, May 1982, pp. 580-586.

Gonzalez, "Digital Image Fundamentals," Digital Image Processing, Second Edition, 1987, pp. 52-54.

Gottesfeld Brown et al., "Registration of Planar Film Radiographs with Computer Tomography," Proceedings of MMBIA, Jun. 96, pp. 42-51.

Gueziec et al., "Registration of Computed Tomography Data to a Surgical Robot Using Fluoroscopy: A Feasibility Study," Computer Science/Mathematics, Sep. 27, 1996, 6 pages.

Hamadeh et al, "Kinematic Study of Lumbar Spine Using Functional Radiographies and 3D/2D Registration," TIMC UMR 5525—IMAG, undated.

Hamadeh et al., "Automated 3-Dimensional Computed Tomographic and Fluorscopic Image Registration," Computer Aided Surgery (1998), 3:11-19.

Hatch, "Reference-Display System for the Integration of CT Scanning and the Operating Microscope," Thesis, Thayer School of Engineering, Oct. 1984, pp. 1-189.

Heilbrun et al., "Preliminary experience with Brown-Roberts-Wells (BRW) computerized tomography stereotaxic guidance system," Journal of Neurosurgery, vol. 59, Aug. 1983, pp. 217-222.

Henderson et al., "An Accurate and Ergonomic Method of Registration for Image-guided Neurosurgery," Computerized Medical Imaging and Graphics, vol. 18, No. 4, Jul.-Aug. 1994, pp. 273-277.

Hoerenz, "The Operating Microscope I. Optical Principles, Illumination Systems, and Support Systems," Journal of Microsurgery, vol. 1, 1980, pp. 364-369.

Hofstetter et al., "Fluoroscopy Based Surgical Navigation—Concept and Clinical Applications," Computer Assisted Radiology and Surgery, 1997, pp. 956-960.

Horner et al., "A Comparison of CT-Stereotaxic Brain Biopsy Techniques," Investigative Radiology, Sep.-Oct. 1984, pp. 367-373.

Hounsfield, "Computerized transverse axial scanning (tomography): Part 1. Description of system," British Journal of Radiology, vol. 46, No. 552, Dec. 1973, pp. 1016-1022.

Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.

* cited by examiner

METHOD AND APPARATUS FOR SURGICAL NAVIGATION

FIELD

The present invention relates generally to navigated surgery, and more specifically, to systems and methods for using instruments and systems to assist in navigating surgical procedures in internal body structures.

BACKGROUND

Image guided medical and surgical procedures utilize patient images obtained prior to or during a medical procedure to guide a physician performing the procedure. Recent advances in imaging technology, especially in imaging technologies that produce highly-detailed, two, three, and four dimensional images, such as computed tomography (CT), magnetic resonance imaging (MRI), fluoroscopic imaging (such as with a C-arm device), positron emission tomography (PET), and ultrasound imaging (US) has increased the interest in image guided medical procedures.

Typical image guided navigation systems generally require dynamic reference frames to track the position of the patient should patient movement occur during the assisted procedure. The dynamic reference frame is generally affixed to the patient in a generally permanent or immovable fashion. The dynamic reference frame may also be used as a fiducial marker and may, therefore, be attached to the patient during the acquisition of pre-operative images. This enables the image space to be aligned with patient space during the navigated procedure. For example, with relation to a cranial procedure, the dynamic reference frame can be attached to the skull by a bone screw. For other procedures the dynamic reference frame may be fixed to other boney portions also with bone screws. Regardless, the dynamic reference frame may include a portion that is fixed to the patient during the acquisition of the pre-operative images and remains attached until the procedure is complete to insure proper and accurate correlation between image space and patient space. Requiring that the dynamic reference frame be attached to the patient during the time that the pre-acquired images are acquired until the procedure actually takes place may be uncomfortable.

The dynamic reference frame may, then be used to assure that images of a patient, such as pre-acquired or atlas images, may be registered to the patient space. Generally this registration also allows for tracking of various instruments during a procedure. The tracked instruments will generally include portions that may be tracked and superimposed over acquired or modeled images of the patient.

Various instruments may be used during an operative procedure that are desired to be tracked. Even if images are acquired, either intra-operatively or pre-operatively, the instrument is generally illustrated, and superimposed on the captured image data to identify the position of the instrument relative to the patient space. Therefore, the instrument may include detectable portions, such as electromagnetic coils or optical detection points, such as LEDs or reflectors, that may be detected by a suitable navigation system.

Size considerations generally make it difficult to position the tracking sensors near a portion of the instrument to be positioned within the patient, such as the distal tip. Because of this, the tracking sensors are generally positioned within the handle of the instrument. Therefore, complex calculations and a degree of error may exist to determine the exact position of a distal end of the instrument relative to the position of the detectable sensors. Also the instruments may flex unexpectedly so that the known dimensions are no longer true dimensions of the instrument. Therefore, it may be desirable to provide sensors substantially near the distal tip or end of an instrument positioned within a patient.

The tracking of various sensor portions, such as electromagnetic coils, may require the transmission of a current or a voltage to or from the sensors. Therefore, an electrical potential is provided to an instrument that is often positioned within a portion of the patient's anatomy, which may include various portions such as the cardiac area, neurological area, and other areas of the patient. In order to provide separation of these potentials from the patient, it may also be desirable to isolate the potentials from the patient.

SUMMARY

A surgical navigation system for navigating a region of a patient includes a non-invasive dynamic reference frame and/or fiducial marker, sensor tipped instruments, and isolator circuits. The dynamic reference frame may be repeatably placed on the patient in a non-invasive manner and in a precise location for guiding the instruments. The instruments may be precisely guided by positioning sensors near moveable portions of the instruments. The patient may be electrically isolated from various sources of current during the procedure.

According to various embodiments a surgical navigation system includes a method of forming an electromagnetic sensing coil in a medical instrument. The method may include forming a core of a conductive material and forming a coil about the core. The core is covered with a first layer of a material and a second layer of a material may also cover the core, and at least part of the first layer. The coil may be substantially electrically isolated from the core.

According to various embodiment a surgical navigation system for a substantially minimally invasive dynamic reference frame is disclosed. The dynamic reference frame may include a body portion selectively attachable to a portion of the anatomy. It may also include a navigation portion to at least one of sense and transmit a characteristic. A holding section is able to hold the body portion relative to the portion of the anatomy. The holding section may substantially non-invasively holds the body portion relative to the portion of the anatomy.

According to various embodiments a surgical navigation system for navigating a procedure relative to a patient having an electrical isolating portion. The navigation system may include an electrical source and an instrument including a conducting element disposable near the patient. A transmission medium may interconnect the electrical source and the instrument. An electrical isolator may electrically isolate the instrument from the electrical source.

Further areas of applicability will become apparent from the detailed description provided hereinafter. It should be understood that the detailed description and various examples, while indicating various embodiments, are intended for purposes of illustration only and are not intended to limit the scope of the description or the appended claims.

BRIEF DESCRIPTION OF THE DRAWINGS

The present invention will become more fully understood from the detailed description and the accompanying drawings, wherein.

DETAILED DESCRIPTION OF THE VARIOUS EMBODIMENTS

The following description of the various embodiments is merely exemplary in nature and is in no way intended to limit the invention, its application, or uses. As indicated above, the present invention is directed at providing improved, non-line-of-site image-guided navigation of an instrument, such as a stylet, probe, suction tube, catheter, balloon catheter, implant, lead, stent, needle, guide wire, insert and/or capsule, that may be used for physiological monitoring, delivering a medical therapy, or guiding the delivery of a medical device, orthopedic implant, or soft tissue implant in an internal body space to any region of the body.

Figure 1:
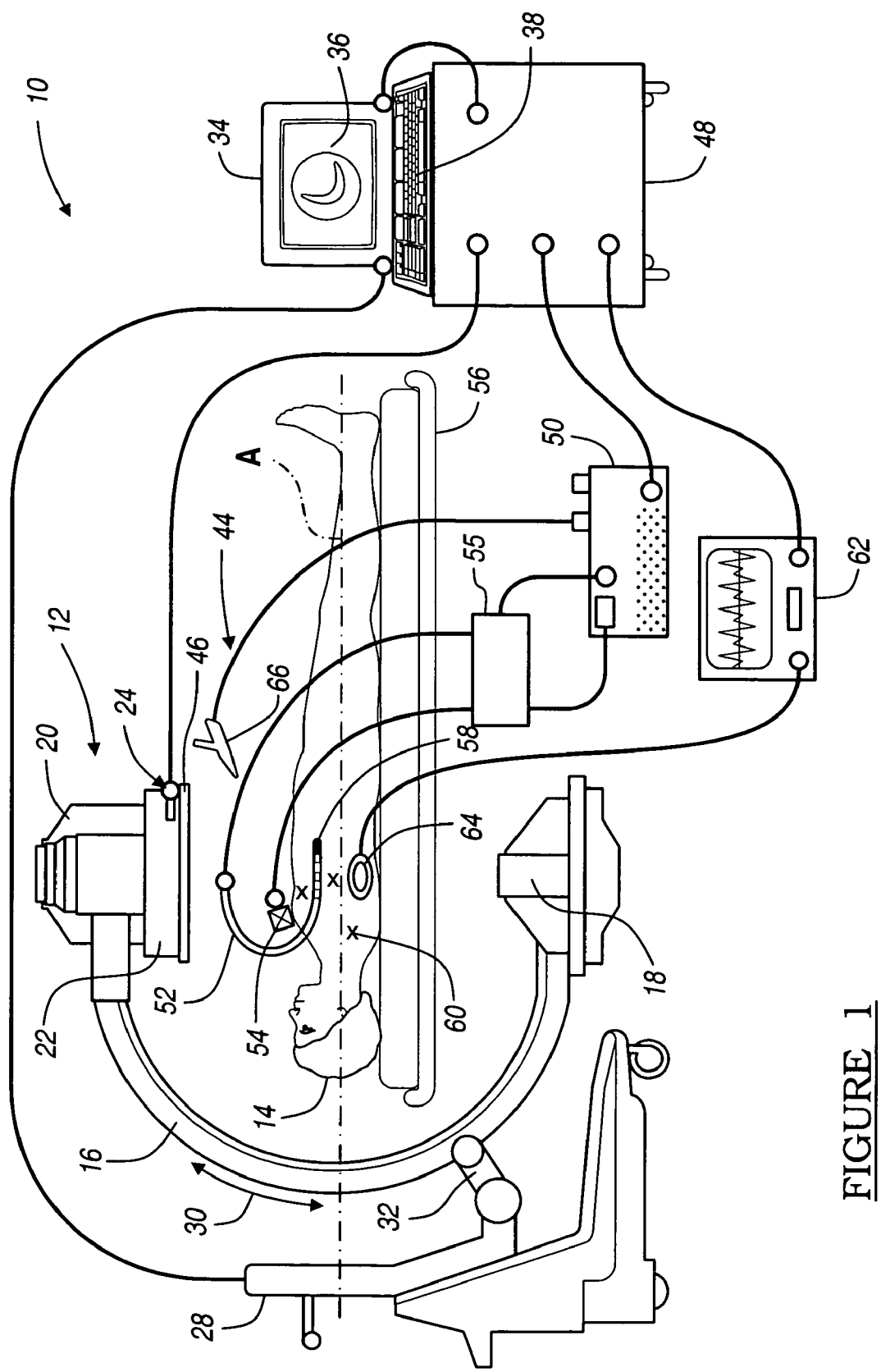
FIG. 1 is a diagram of a navigation system according to various teachings of the present invention.

FIG. 1 is a diagram illustrating an overview of an image-guided navigation system 10 for use in non-line-of-site navigating of an instrument. It should further be noted that the navigation system 10 may be used to navigate any type of instrument, implant or delivery system, including guide wires, needles, drug delivery systems, cell delivery systems, gene delivery systems, biopsy systems, arthroscopic systems, etc. Moreover, these instruments may be used to navigate or map any regions of the body.

The navigation system 10 may include an optional imaging device 12 that is used to acquire pre-, intra-, or post-operative or real-time images of a patient 14. The optional imaging device 12 is, for example, a fluoroscopic x-ray imaging device that may include a C-arm 16 having an x-ray source 18, an x-ray receiving section 20, an optional calibration and tracking target 22 and optional radiation sensors 24. The calibration and tracking target 22 includes calibration markers 26 (see FIGS. 2A-2B), further discussed herein. A C-arm, or optional imaging device controller 28 captures the x-ray images received at the receiving section 20 and stores the images for later use. The C-arm controller 28 may also be separate from the C-arm 16 and/or control the rotation of the C-arm 16. For example, the C-arm 16 may move in the direction of arrow 30 or rotates about a longitudinal axis 14a of the patient 14, allowing anterior or lateral views of the patient 14 to be imaged. Each of these movements involve rotation about a mechanical axis 32 of the C-arm 16. In this example, the longitudinal axis 14a of the patient 14 is substantially in line with the mechanical axis 32 of the C-arm 16. This enables the C-arm 16 to be rotated relative to the patient 14, allowing images of the patient 14 to be taken from multiple directions or about multiple planes. An example of a fluoroscopic C-arm x-ray that may be used as the optional imaging device 12 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc.

In operation, the imaging device 12 generates x-rays from the x-ray source 18 that propagate through the patient 14 and calibration and/or tracking target 22, into the x-ray receiving section 20. The receiving section 20 generates an image representing the intensities of the received x-rays. Typically, the receiving section 20 includes an image intensifier that first converts the x-rays to visible light and a charge coupled device (CCD) video camera that converts the visible light into digital images. Receiving section 20 may also be a digital device that converts x-rays directly to digital images, thus potentially avoiding distortion introduced by first converting to visible light. With this type of digital C-arm, which is generally a flat panel device, the optional calibration and/or tracking target 22 and the calibration process discussed below may be eliminated. Also, the calibration process may be eliminated or not used at all for cardiac therapies. Alternatively, the imaging device 12 may only take a single image with the calibration and tracking target 22 in place. Thereafter, the calibration and tracking target 22 may be removed from the line-of-sight of the imaging device 12.

Two dimensional fluoroscopic images that may be taken by the optional imaging device 12 are captured and stored in the C-arm controller 28. Multiple two-dimensional images taken by the imaging device 12 may also be captured and assembled to provide a larger view or image of a whole region of a patient, as opposed to being directed to only a portion of a region of the patient. For example, multiple image data of a patient's leg may be appended together to provide a full view or complete set of image data of the leg that can be later used to follow contrast agent, such as Bolus tracking.

These images are then forwarded from the C-arm controller 28 to a navigation computer controller or work station 34 having a display 36 and a user interface 38. It will also be understood that the images are not necessarily first retained in the controller 28, but may also be directly transmitted to the navigation computer 34. The work station 34 provides facilities for displaying on the display 36, saving, digitally manipulating, or printing a hard copy of the received images. The user interface 38, which may be a keyboard, mouse, touch pen, touch screen or other suitable device, allows a physician or user to provide inputs to control the imaging device 12, via the C-arm controller 28, or adjust the display settings of the display 36. The work station 34 may also direct the C-arm controller 28 to adjust the rotational axis 32 of the C-arm 16 to obtain various two-dimensional images along different planes in order to generate representative two-dimensional and three-dimensional images.

When the x-ray source 18 generates the x-rays that propagate to the x-ray receiving section 20, the radiation sensors 24 sense the presence of radiation, which is forwarded to the C-arm controller 28, to identify whether or not the imaging device 12 is actively imaging. This information is also transmitted to a coil array controller 48, further discussed herein. Alternatively, a person or physician may manually indicate when the imaging device 12 is actively imaging or this function can be built into the x-ray source 18, x-ray receiving section 20, or the control computer 28.

Figure 2B:
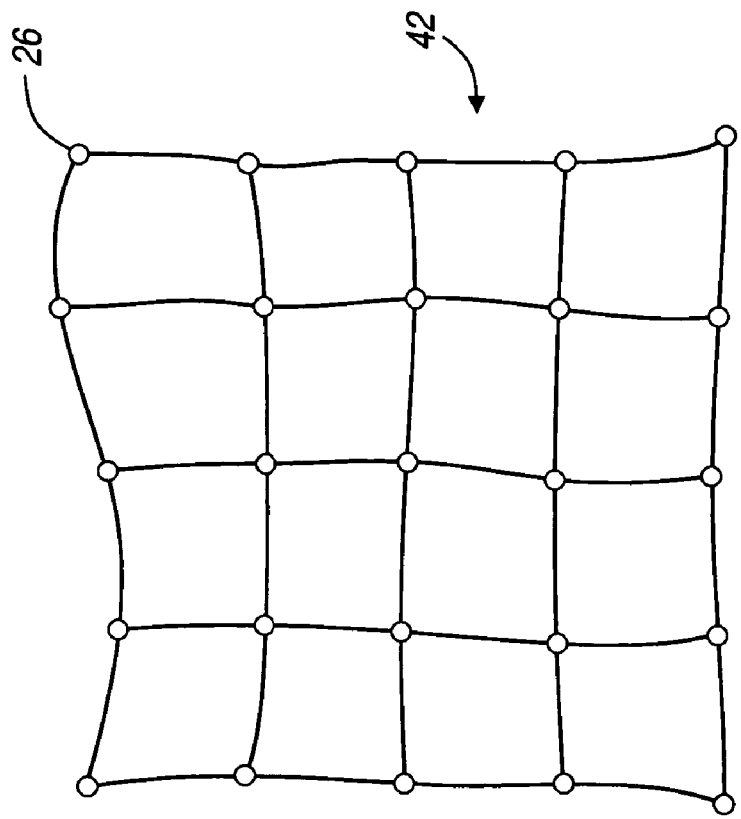
FIGS. 2A and 2B are diagrams representing undistorted and distorted views from a fluoroscopic C-arm imaging device.
Figure 2A:
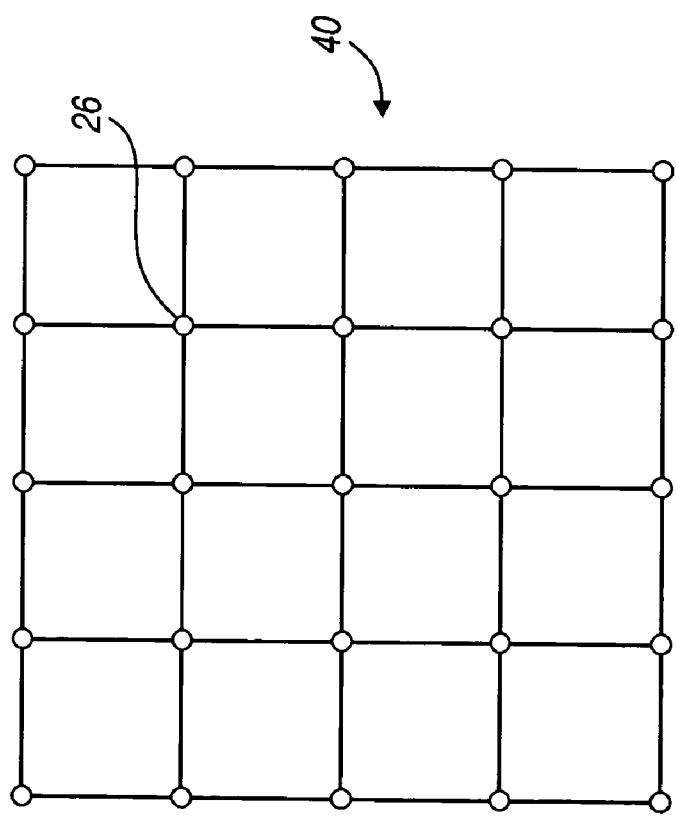

The optional imaging device 12, such as the fluoroscopic C-arm 16, that do not include a digital receiving section 20 generally require the optional calibration and/or tracking target 22. This is because the raw images generated by the receiving section 20 tend to suffer from undesirable distortion caused by a number of factors, including inherent image distortion in the image intensifier and external electromagnetic fields. An empty undistorted or ideal image and an empty distorted image are shown in FIGS. 2A and 2B, respectively. The checkerboard shape, shown in FIG. 2A, represents the ideal image 40 of the checkerboard arranged calibration markers 26. The image taken by the receiving section 20, however, can suffer from distortion, as illustrated by the distorted calibration marker image 42, shown in FIG. 2B.

Intrinsic calibration, which is the process of correcting image distortion in a received image and establishing the projective transformation for that image, involves placing the calibration markers 26 in the path of the x-ray, where the calibration markers 26 are opaque or semi-opaque to the x-rays. The calibration markers 26 are rigidly arranged in pre-determined patterns in one or more planes in the path of the x-rays and are visible in the recorded images. Because the true relative position of the calibration markers 26 in the recorded images are known, the C-arm controller 28 or the work station or computer 34 is able to calculate an amount of distortion at each pixel in the image (where a pixel is a single point in the image). Accordingly, the computer or work station 34 can digitally compensate for the distortion in the image and generate a distortion-free or at least a distortion improved image 40 (see FIG. 2A). A more detailed explanation of exemplary methods for performing intrinsic calibration are described in the references: B. Schuele, et al., "Correction of Image Intensifier Distortion for Three-Dimensional Reconstruction," presented at SPIE Medical Imaging, San Diego, Calif., 1995; G. Champleboux, et al., "Accurate Calibration of Cameras and Range Imaging Sensors: the NPBS Method," Proceedings of the IEEE International Conference on Robotics and Automation, Nice, France, May, 1992; and U.S. Pat. No. 6,118,845, entitled "System And Methods For The Reduction And Elimination Of Image Artifacts In The Calibration Of X-Ray Imagers," issued Sep. 12, 2000, the contents of which are each hereby incorporated by reference.

While the optional imaging device 12 is shown in FIG. 1, any other alternative 2D, 3D or 4D imaging modality may also be used. For example, any 2D, 3D or 4D imaging device, such as isocentric fluoroscopy, bi-plane fluoroscopy, ultrasound, computed tomography (CT), multi-slice computed tomography (MSCT), magnetic resonance imaging (MRI), high frequency ultrasound (HIFU), positron emission tomography (PET), optical coherence tomography (OCT), intra-vascular ultrasound (IVUS), ultrasound, intra-operative CT or MRI may also be used to acquire 2D, 3D or 4D pre- or post-operative and/or real-time images or image data of the patient 14. The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities. A more detailed discussion on optical coherence tomography (OCT), is set forth in U.S. Pat. No. 5,740,808, issued Apr. 21, 1998, entitled "Systems And Methods For Guilding Diagnostic Or Therapeutic Devices In Interior Tissue Regions" which is hereby incorporated by reference.

Image datasets from hybrid modalities, such as positron emission tomography (PET) combined with CT, or single photon emission computer tomography (SPECT) combined with CT, could also provide functional image data superimposed onto anatomical data to be used to confidently reach target sights within the patient 14. It should further be noted that the optional imaging device 12, as shown in FIG. 1, provides a virtual bi-plane image using a single-head C-arm fluoroscope as the optional imaging device 12 by simply rotating the C-arm 16 about at least two planes, which could be orthogonal planes to generate two-dimensional images that can be converted to three-dimensional volumetric images. By acquiring images in more than one plane, an icon representing the location of a catheter, stylet, suction-probe, or other instrument, introduced and advanced in the patient 14, may be superimposed in more than one view on display 36 allowing simulated bi-plane or even multi-plane views, including two and three-dimensional views.

These types of imaging modalities may provide certain distinct benefits for their use. For example, magnetic resonance imaging (MRI) is generally performed pre-operatively using a non-ionizing field. This type of imaging provides very good tissue visualization in three-dimensional form and also provides anatomy and functional information from the imaging. MRI imaging data is generally registered and compensated for motion correction using dynamic reference frames (DRF) discussed further herein.

Positron emission tomography (PET) imaging is generally a pre-operative imaging procedure that exposes the patient to some level of radiation to provide a 3D image. PET imaging provides functional information and also generally requires registration and motion correction using dynamic reference frames.

Computed tomography (CT) imaging is also generally a pre-operative technique that exposes the patient to a limited level of radiation. CT imaging, however, is a very fast imaging procedure. A multi-slice CT system provides 3D images having good resolution and anatomy information. Again, CT imaging is generally registered and needs to account for motion correction, via dynamic reference frames.

Fluoroscopy imaging is generally an intra-operative imaging procedure that exposes the patient to certain amounts of radiation to provide either two-dimensional or rotational three-dimensional images. Fluoroscopic images generally provide good resolution and anatomy information.

Fluoroscopic images can be either manually or automatically registered and also need to account for motion correction using dynamic reference frames.

Ultrasound imaging is also generally intra-operative procedure using a non-ioning field to provide either 2D, 3D, or 4D imaging, including anatomy and blood flow information. Ultrasound imaging provides automatic registration and does not need to account for any motion correction.

With continuing reference to FIG. 1, the navigation system 10 further includes an electromagnetic navigation or tracking system 44 that includes a transmitter coil array 46, the coil array controller 48, a navigation probe interface 50, an electromagnetic instrument, such as a stylet or catheter 52 and a dynamic reference frame 54. Further included in the navigation system 10 is an isolator circuit or box 55. The isolator circuit or box 55 may be included in a transmission line or interrupt a line carrying a signal or a voltage to the navigation probe interface 50. Alternatively, the isolator circuit included in the isolator box 55 may be included in the navigation probe interface 50, the instrument 52, the dynamic reference frame 54, the transmission lines coupling the devices, or any other appropriate location. As discussed herein, the isolator box 55 is operable to isolate any of the instruments or patient coincidence instruments or portions that are in contact with the patient should an undesirable electrical surge or voltage take place, further discussed herein.

It should further be noted that the entire tracking system 44 or parts of the tracking system 44 may be incorporated into the imaging device 12, including the work station 34 and radiation sensors 24. Incorporating the tracking system 44 may provide an integrated imaging and tracking system. Any combination of these components may also be incorporated into the imaging system 12, which again can include a fluoroscopic C-arm imaging device or any other appropriate imaging device.

The transmitter coil array 46 is shown attached to the receiving section 20 of the C-arm 16. It should be noted, however, that the transmitter coil array 46 may also be positioned at any other location as well. For example, the transmitter coil array 46 may be positioned at the x-ray source 18, within or atop the OR table 56 positioned below the patient 14, on siderails associated with the table 56, or positioned on the patient 14 in proximity to the region being navigated, such as on the patient's chest. The transmitter coil array 46 may also be positioned in the items being navigated, further discussed herein. The transmitter coil array 46 includes a plurality of coils that are each operable to generate distinct electromagnetic fields into the navigation region of the patient 14, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The transmitter coil array 46 is controlled or driven by the coil array controller 48. The coil array controller 48 drives each coil in the transmitter coil array 46 in a time division multiplex or a frequency division multiplex manner. In this regard, each coil may be driven separately at a distinct time or all of the coils may be driven simultaneously with each being driven by a different frequency. Upon driving the coils in the transmitter coil array 46 with the coil array controller 48, electromagnetic fields are generated within the patient 14 in the area where the medical procedure is being performed, which is again sometimes referred to as patient space. The electromagnetic fields generated in the patient space induce currents in sensors 58 positioned in the instrument 52, such as the catheter, further discussed herein. These induced signals from the instrument 52 are delivered to the navigation probe interface 50 through the isolation circuit 55 and subsequently forwarded to the coil array controller 48. The navigation probe interface 50 may provide all the necessary electrical isolation for the navigation system 10. Alternatively, the electrical isolation may also be provided in the isolator box 55. Nevertheless, as mentioned here, the isolator assembly 55 may be included in the navigation probe interface 50 or may be integrated into the instrument 52, and any other appropriate location. The navigation probe interface 50 also includes amplifiers, filters and buffers required to directly interface with the sensors 58 in the instrument 52. Alternatively, the instrument 52 may employ a wireless communications channel as opposed to being coupled directly to the navigation probe interface 50.

The instrument 52, as will be described in detail below, is equipped with at least one, and generally multiple, localization sensors 58. The instrument 52 can be a steerable catheter that includes a handle at a proximal end and the multiple location sensors 58 fixed to the catheter body and spaced axially from one another along the distal segment of the catheter 52. The catheter 52, as shown in FIG. 1 includes four localization sensors 58. The localization sensors 58 are generally formed as electromagnetic receiver coils, such that the electromagnetic field generated by the transmitter coil array 46 induces current in the electromagnetic receiver coils or sensors 58. The catheter 52 may also be equipped with one or more sensors, which are operable to sense various physiological signals. For example, the catheter 52 may be provided with electrodes for sensing myopotentials or action potentials. An absolute pressure sensor may also be included, as well as other electrode sensors. The catheter 52 may also be provided with an open lumen, further discussed herein, to allow the delivery of a medical device or pharmaceutical/cell/gene agents. For example, the catheter 52 may be used as a guide catheter for deploying a medical lead, such as a cardiac lead for use in cardiac pacing and/or defibrillation or tissue ablation. The open lumen may alternatively be used to locally deliver pharmaceutical agents, cell, or genetic therapies.

In an alternate embodiment, the electromagnetic sources or generators may be located within the instrument 52 and one or more receiver coils may be provided externally to the patient 14 forming a receiver coil array similar to the transmitter coil array 46. In this regard, the sensor coils 58 would generate electromagnetic fields, which would be received by the receiving coils in the receiving coil array similar to the transmitter coil array 46. Other types of localization sensors or systems may also be used, which may include an emitter, which emits energy, such as light, sound, or electromagnetic radiation, and a receiver that detects the energy at a position away from the emitter. This change in energy, from the emitter to the receiver, is used to determine the location of the receiver relative to the emitter. Other types of tracking systems include optical, acoustic, electrical field, RF and accelerometers. Accelerometers enable both dynamic sensing due to motion and static sensing due to gravity. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

The dynamic reference frame 54 of the electromagnetic tracking system 44 is also coupled to the navigation probe interface 50 to forward the information to the coil array controller 48. The dynamic reference frame 54, briefly and discussed in detail according to various embodiments herein, is a small magnetic field detector that is designed to be fixed to the patient 14 adjacent to the region being navigated so that any movement of the patient 14 is detected as relative motion between the transmitter coil array 46 and the dynamic reference frame 54. This relative motion is forwarded to the coil array controller 48, which updates registration correlation and maintains accurate navigation, further discussed herein. The dynamic reference frame 54 can be configured as a pair of orthogonally oriented coils, each having the same center or may be configured in any other non-coaxial or co-axial coil configuration. The dynamic reference frame 54 may be affixed externally to the patient 14, adjacent to the region of navigation, such as on the patient's chest, as shown in FIG. 1. The dynamic reference frame 54 can be affixed to the patient's skin, by way of a selected adhesive patch and/or a tensioning system. The dynamic reference frame 54 may also be removably attachable to fiducial markers 60 also positioned on the patient's body and further discussed herein.

Alternatively, the dynamic reference frame 54 may be internally attached, for example, to the wall of the patient's heart or other soft tissue using a temporary lead that is attached directly to the heart. This provides increased accuracy since this lead may track the regional motion of the heart. Gating may also increase the navigational accuracy of the system 10. Gating procedures may be particular important when performing procedures relative to portions of the anatomy that move on a regular basis, such as the heart or the lungs or diaphragm. Although, it is not necessary to provide gating, it may be selected to do so during various procedures. Various gating procedures and techniques are described, such as U.S. patent application Ser. No. 10/619,216 entitled Navigation "System For Cardiac Therapies" filed on Jul. 14, 2003, and incorporated herein by reference. Dynamic reference frame 54 according to various embodiments and a fiducial marker 60, are set forth in U.S. Pat. No. 6,381,485, entitled "Registration of Human Anatomy Integrated for Electromagnetic Localization," issued Apr. 30, 2002, which is hereby incorporated by reference.

It should further be noted that multiple dynamic reference frames 54 may also be employed. For example, an external dynamic reference frame 54 may be attached to the chest of the patient 14, as well as to the back of the patient 14. Since certain regions of the body may move more than others due to motions of the heart or the respiratory system, each dynamic reference frame 54 may be appropriately weighted to increase accuracy even further. In this regard, the dynamic reference frame 54 attached to the back may be weighted higher than the dynamic reference frame 54 attached to the chest, since the dynamic reference frame 54 attached to the back is relatively static in motion.

The navigation system 10 may optionally further include a gating device 62 such as an ECG or electrocardiogram, which is attached to the patient 14, via skin electrodes 64, and in communication with the coil array controller 48. Respiration and cardiac motion can cause movement of cardiac structures relative to the instrument 52, even when the instrument 52 has not been moved. Therefore, localization data may be acquired on a time-gated basis triggered by a physiological signal. For example, the ECG or EGM signal may be acquired from the skin electrodes 64 or from a sensing electrode included on the instrument 52 or from a separate reference probe. A characteristic of this signal, such as an R-wave peak or P-wave peak associated with ventricular or atrial depolarization, respectively, may be used as a triggering event for the coil array controller 48 to drive the coils in the transmitter coil array 46. This triggering event may also be used to gate or trigger image acquisition during the imaging phase with the imaging device 12. By time-gating or event gating at a point in a cycle the image data and/or the navigation data, the icon of the location of the catheter 52 relative to the heart at the same point in the cardiac cycle may be displayed on the display 36, such as disclosed in U.S. patent application Ser. No. 10/619,216, entitled "Navigation System For Cardiac Therapies" filed on Jul. 14, 2003.

Additionally or alternatively, a sensor regarding respiration may be used to trigger data collection at the same point in the respiration cycle. Additional external sensors can also be coupled to the navigation system 10. These could include a capnographic sensor that monitors exhaled $CO_2$ concentration. From this, the end expiration point can be easily determined. The respiration, both ventriculated and spontaneous causes an undesirable elevation or reduction (respectively) in the baseline pressure signal. By measuring systolic and diastolic pressures at the end expiration point, the coupling of respiration noise is minimized. As an alternative to the $CO_2$ sensor, an airway pressure sensor can be used to determine end expiration.

Briefly, the navigation system 10 operates as follows. The navigation system 10 creates a translation map between all points in the radiological image generated from the imaging device 12 and the corresponding points in the patient's anatomy in patient space. After this map is established, whenever a tracked instrument, such as the catheter 52 or a pointing device 66 is used, the work station 34 in combination with the coil array controller 48 and the C-arm controller 28 uses the translation map to identify the corresponding point on the pre-acquired image or atlas model, which is displayed on display 36. This identification is known as navigation or localization. An icon representing the localized point or instruments are shown on the display 36 within several two-dimensional image planes, as well as on three and four dimensional images and models.

To enable navigation, the navigation system 10 must be able to detect both the position of the patient's anatomy and the position of the catheter 52 or other surgical instrument. Knowing the location of these two items allows the navigation system 10 to compute and display the position of the catheter 52 in relation to the patient 14. The tracking system 44 is employed to track the catheter 52 and the anatomy simultaneously.

The tracking system 44 essentially works by positioning the transmitter coil array 46 adjacent to the patient space to generate a low-energy magnetic field generally referred to as a navigation field. Because every point in the navigation field or patient space is associated with a unique field strength, the electromagnetic tracking system 44 can determine the position of the catheter 52 by measuring the field strength at the sensor 58 location. The dynamic reference frame 54 is fixed to the patient 14 to identify the location of the patient in the navigation field. The electromagnetic tracking system 44 continuously recomputes the relative position of the dynamic reference frame 54 and the catheter 52 during localization and relates this spatial information to patient registration data to enable image guidance of the catheter 52 within the patient 14.

Patient registration is the process of determining how to correlate the position of the instrument or catheter 52 on the patient 14 to the position on the diagnostic or pre-acquired images. To register the patient 14, the physician or user may use point registration by selecting and storing particular points from the pre-acquired images and then touching the corresponding points on the patient's anatomy with the pointer probe 66. The navigation system 10 analyzes the relationship between the two sets of points that are selected and computes a match, which correlates every point in the image data with its corresponding point on the patient's anatomy or the patient space. The points that are selected to perform registration are the fiducial markers or landmarks 60, such as anatomical landmarks. Again, the landmarks or fiducial points 60 are identifiable on the images and identifiable and accessible on the patient 14. The landmarks 60 can be artificial landmarks 60 that are positioned on the patient 14 or anatomical landmarks that can be easily identified in the image data. The artificial landmarks, such as the fiducial markers 60, can also form part of the dynamic reference frame 54.

The system 10 may also perform registration using anatomic surface information or path information as is known in the art. The system 10 may also perform 2D to 3D registration by utilizing the acquired 2D images to register 3D volume images by use of contour algorithms, point algorithms or density comparison algorithms, as is known in the art. An exemplary 2D to 3D registration procedure, as set forth in U.S. Ser. No. 60/465,615, entitled "Method and Apparatus for Performing 2D to 3D Registration" filed on Apr. 25, 2003, which is hereby incorporated by reference. The registration process may also be synched to an anatomical function, for example, by the use of the ECG device 62.

In order to maintain registration accuracy, the navigation system 10 continuously tracks the position of the patient 14 during registration and navigation. This is because the patient 14, dynamic reference frame 54, and transmitter coil array 46 may all move during the procedure, even when this movement is not desired. Therefore, if the navigation system 10 did not track the position of the patient 14 or area of the anatomy, any patient movement after image acquisition would result in inaccurate navigation within that image. The dynamic reference frame 54 allows the electromagnetic tracking device 44 to register and track the anatomy. Because the dynamic reference frame 54 is rigidly fixed to the patient 14, any movement of the anatomy or the transmitter coil array 46 is detected as the relative motion between the transmitter coil array 46 and the dynamic reference frame 54. This relative motion is communicated to the coil array controller 48, via the navigation probe interface 50, which updates the registration correlation to thereby maintain accurate navigation.

The navigation system 10 can be used according to any appropriate method or system. For example, pre-acquired images or atlas or 3D models may be registered relative to the patient and patient space. Various registration regimens and techniques include those described in U.S. patent application Ser. No. 10/619,216 entitled "Navigation System For Cardiac Therapies" filed on Jul. 14, 2003. Generally, the registration system allows the images on the display 36 to be registered and accurately display the real time location of the various instruments, such as the instrument 52, and other appropriate items, such as the pointer 66. In addition, the pointer 66 may be used to register the patient space to the pre-acquired images or the atlas or 3D models. In addition, the dynamic reference frame 54 may be used to ensure that any planned or unplanned movement of the patient or the receiver array 46 is determined and used to correct the image on the display 36.

Figure 3:
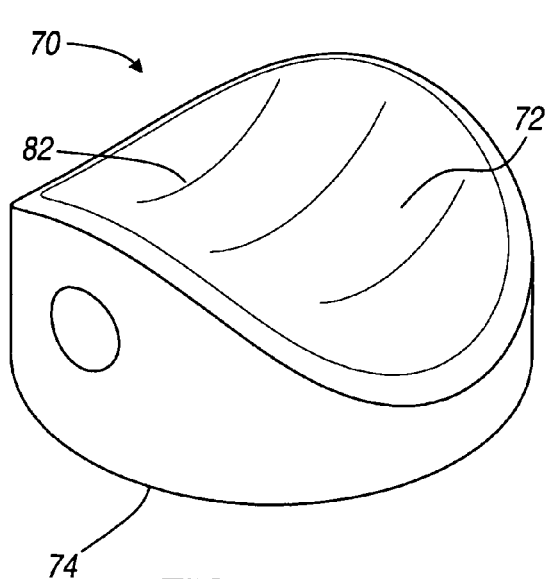
FIG. 3 is a top perspective view of a non-invasive dynamic reference frame according to various embodiments.

As discussed above, the dynamic reference frame 54 may include any appropriate dynamic reference frame, such as the selectively fixable dynamic reference frame 70 illustrated in FIG. 3. The dynamic reference frame 70 generally includes a superior side 72 and an inferior side 74.

Figure 4:
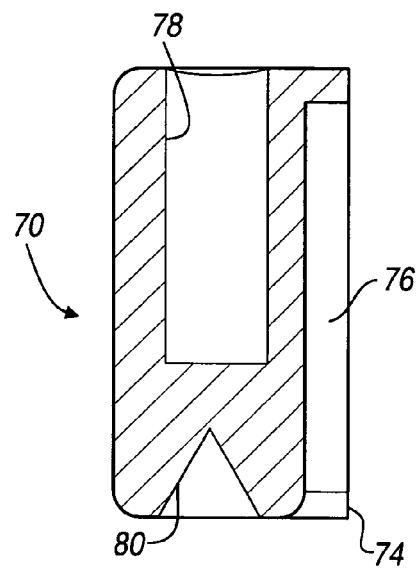
FIG. 4 is a cross-sectional view of the non-invasive dynamic reference frame of FIG. 3.

With continuing reference to FIG. 3 and additional reference to FIG. 4, the dynamic reference frame 70 includes a recess 76 as a portion of the inferior side 74. The recess 76 may be provided for any appropriate purpose, such as receiving a selective adhesive. In addition, as discussed herein, the recess may be used to allow the gathering of soft tissue relative to the dynamic reference frame 70. As described, the dynamic reference frame 70 may be affixed to the patient 14 in any appropriate position.

An adhesive positioned in the adhesive recess 76 generally allows the dynamic reference frame 70 to be fixed to the selected point on the patient 14. As discussed further herein, a tensioning apparatus may also be provided on the dynamic reference frame 70 to further assist holding the dynamic reference frame in a selected position. Further, the dynamic reference frame 70 defines a bore 78 to removably receive a selected sensor or coil. As described herein, the sensor may be fitted into the sensor bore 78 and removed from the sensor bore 78 as selected. For example, should the dynamic reference frame 70 also be used as a fiducial marker 60 it may be radio-or image-opaque, and the sensor bobbin 90 may be removed from the bore 78 during imaging of the patient 14, such as acquiring MRI images. This eliminates any distortion that may be caused by the bobbin 90. Nevertheless, the sensor bobbin 90 may also be permanently provided within the sensor bore 78 for ease of use of the apparatus. It may be desirable to provide the dynamic reference frame 70 as a substantially disposable exterior portion and the sensor may be reusable. In either case, the dynamic reference frame 70 may be formed of a plastic or other non-conductive material.

If the dynamic reference frame 70 is used as a fiducial marker, the dynamic reference frame 70 may define a localization divot 80. The divot or recess 80 allows the pointer 66 or any appropriate mechanism to determine the location of the dynamic reference frame 70 relative to the patient 14 or the patient space. Generally, the pointer 66 is able to engage the divot 80 in a selected manner in patient space, such that the navigation system 44 is able to determine the position of the dynamic reference frame 70 relative to the patient 14. The pointer 66 is also engaged or used to point out the divot 80 in the pre-acquired image to register the image space with the patient space. Therefore, detected movement of the dynamic reference frame 70 may be used to determine movement of the patient 14. It will be understood that the divot 80 may be positioned in any appropriate portion of the dynamic reference frame 70 but is generally provided in an easily accessible and viewable area. moreover, there may be multiple divots 80 or landmarks, as discussed herein. The multiple divots 80 may be used as fiducial markers. There dynamic reference frame 70 may also include a radio-opaque material to be imaged in various imaging techniques.

With further reference to FIG. 3, the dynamic reference frame 70 may include a concave recess 82 defined as a portion of the superior part 72 of the dynamic reference frame 70. The recess 82 may be provided for any appropriate purpose such as engaging a tensioning member 84. The tensioning member 84 may include an adhesive strip that is applied relative to the dynamic reference frame 70 to ensure a substantial selected fixation of the dynamic reference frame 70 relative to the patient 14.

Figure 5:
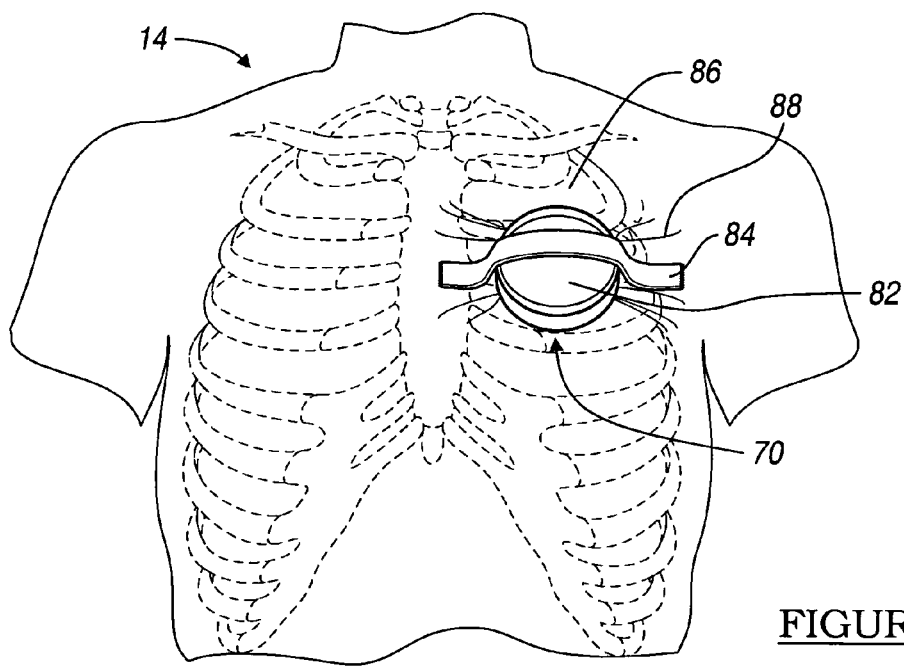
FIG. 5 is an environmental application of the non-invasive dynamic reference frame of FIG. 3.
Figure 6:
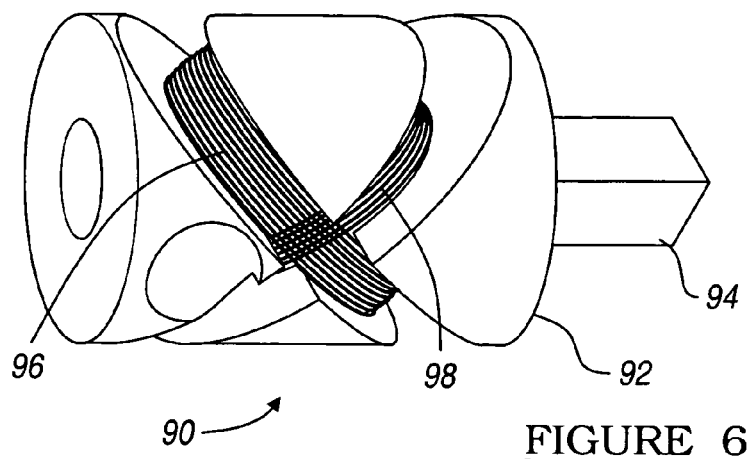
FIG. 6 is a sensor bobbin that may be used in the non-invasive dynamic reference frame of FIG. 3.

With reference to FIG. 5, an exemplary use of the dynamic reference frame 70 is illustrated. The dynamic reference frame 70 is affixed to the patient 14 using an adhesive that is included in the adhesive recess 76. In addition, the tensioning strip 84 is placed atop the recess 82 to further hold the dynamic reference frame 70. The tensioning strip 84 helps by tensioning the dermis 86 of the patient 84 relative to the dynamic reference frame 70. Generally, the dermis 86 will form pucker or tension lines 88 to illustrate or ensure that the dynamic reference frame 70 is substantially fixed to the patient 14. In this way, the soft tissue to which the dynamic reference frame 70 is fixed and is not able to move relative to the dynamic reference frame 70, thereby providing a relatively stable and secure attachment to the patient 14.

Although it is illustrated that the dynamic reference frame 70 may be tensioned relative to the skin of the pectoral region of the patient the dynamic reference frame 70 may be tensioned relative to any appropriate portion of the anatomy. For example, the dynamic reference frame 70 may be fixed relative to a posterior portion of the patient 14 relative to the spine, if a spinal procedure is occurring. In addition, the dynamic reference frame 70 may be tensioned to the dermis on the forehead of the patient, if a procedure relative to the cranium is being performed. Nevertheless, the dynamic reference frame 70 may be fixed to the dermis with substantial force using the tensioning device 84.

Although the tensioning device 84 is illustrated to be a separate strip of material having an adhesive, it will be understood that the tensioning device 84 may be integrated into the dynamic reference frame 70. For example, a tensioning system may be fixed to the superior portion 72 of the dynamic reference frame 70 and a backing released to expose an adhesive region to allow the tensioning system to tension the dermis relative to the dynamic reference frame 70. In addition, tensioning strips, that form the tensioning device 84 may be affixed to or formed integrally with any appropriate portion of the dynamic reference frame 70 to allow for easy use during an operative procedure. For example, tape or a belt may be used that may be separate or integral with the dynamic reference frame 70. Therefore, it will be understood that the tensioning device 84 need not be limited according to any selected embodiments and is provided to allow for tensioning the dermis relative to the dynamic reference frame 70.

As is generally known by one skilled in the art, the dermis of an individual is generally not substantially taught over the sub-dermal anatomy. That is, a portion of the anatomy may move relative to the dermis without the dermis moving. Although this may be desired for general anatomical or natural movements, it may be desired to know the precise movements of any portions of the anatomy of the patient 14 during an operative procedure where the navigation system 44 is being used.

The instrument 52, such as the catheter, may be engaged to a subdermal region of the patient 14. Movement of any subdermal portion may be selected to be known during the operative procedure. In addition, the position of the instrument 52 relative to the subdermal anatomical portions may be selected to be substantially known. Therefore, the dynamic reference frame 70 may be fixed to the patient 14 to allow for ensuring that the image on the display 36 substantially correctly illustrates the position of the anatomy of the patient 14. If subdermal portions are allowed to move without the dynamic reference frame 70 moving, however, it may be possible that the display 36 may not correctly display the proper location of the instrument 52 relative to the subdermal anatomy of the patient 14. Therefore, the tensioning strip 84 may allow for more closely tracking the movement of subdermal portions or portions of the anatomy of the patient 14 without using more invasive techniques.

Generally, the dynamic reference frame 70 may be affixed to the dermis or external portions of the patient 14. This allows the dynamic reference frame 70 to be fixed to the patient and used to reference the position of the patient 14 relative to the position of the other elements, such as the instrument 52 and the pointer 66, and to also ensure the appropriate registration of the images on the display 36 in a substantially non-invasive manner. Simply the dynamic reference frame 70 need not penetrate the dermis to be fixed to a rigid portion of the anatomy, such as a bone portion. Therefore, the dynamic reference frame 70 can be easily fixed and removed from the patient 14 as selected.

An electromagnetic bobbin or multiple coil member 90 may be positioned in the recess 78 of the dynamic reference frame 70. The sensor bobbin 90 includes a body 92 that is generally formed from material that is not conductive to allow the coils to operate and sense a position in a field. In addition, the body 92 may be manipulated by a handle or manipulable portion 94 extending from the body 92. In addition, the handle 94 may allow leads or contacts from an external source, such as illustrated in FIG. 1, to be interconnected to the body portion 92 into the coils 96 and 98.

The first coil 96 and the second coil 98 are generally positioned at angles relative to one another. These angles may be any appropriate angle such as a generally orthogonal angle or other appropriate angle. The two coils 96, 98 being positioned at angles relative to one another, allow for six degrees of freedom sensing including translation, angle, pitch, yaw, and rotation. Therefore, the position or movement of the dynamic reference frame 70 can be determined by sensing the electromagnetic field of the coil array 46 with the first coil 96 and the second coil 98

Generally, the body 92 of the bobbin 90 and the exterior or the bodies of the dynamic reference frame 70 are formed of an appropriate material. For example, the material may be a non-metallic and non-conducting material such as an appropriate ceramic, plastic, and the like. The material may be selected from a material that will not interfere with either transmitting or receiving information regarding the magnetic field and not interfere with imaging of the patient 14. Therefore, the material is a substantially non-conducting material, but may also be visible in the image data.

In addition, the dynamic reference frame 70 may be used to address what may be referred to as skin shift. As described above the skin may move relative to the subdermal anatomic portions. Therefore, the dynamic reference frame 70 may be fixed to the patient 14 in a manner to substantially eliminate error that may be introduced by a skin shift. In addition to the tensioning device 84, the tensioning device may be any appropriate portion. For example, the tensioning device 84 may be a band which substantially extends around the selected anatomical portion of the patient. For example, the dynamic reference frame 70 may be fixed to a band that substantially extends around the chest of a patient during a selected procedure. In addition, the dynamic reference frame 70 may be included on or integral with a band that substantially extends around the cranium, the arm, the thigh, or any other appropriate member. In addition, the band may be substantially elastic to engage the selected anatomical portion. The elastic band may be provided to substantially tension the tissue relative to the dynamic reference frame, but not simply in a localized tensioning manner. The dynamic reference frame 70 can, therefore, be fixed to any appropriate portion of the body either with the localized tensioning member 84 or a non-localized tensioning member. The band may form a general tensioning while a tape portion may form a more localized tensioning. The tensioning members allow for tensioning the dermal tissue over the subdermal anatomy to substantially eliminate skin movement relative to the subdermal area.

Figure 7:
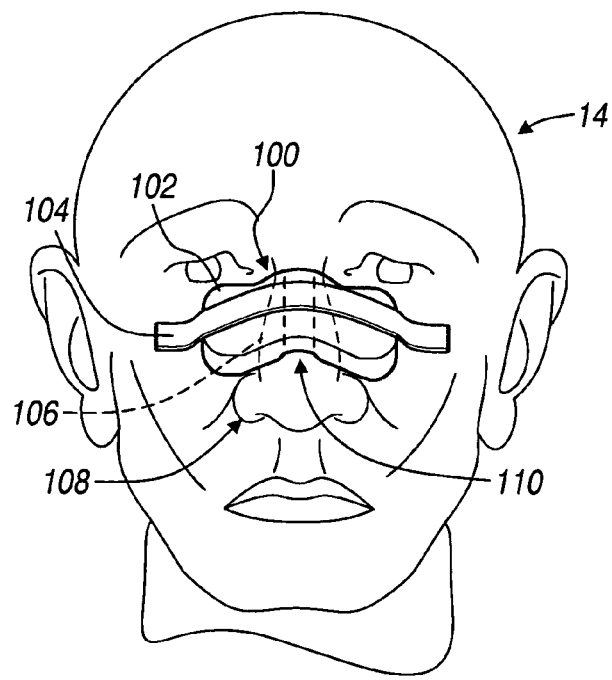
FIG. 7 is an environmental view of another non-invasive dynamic reference frame according to various embodiments.

In addition, the dynamic reference frame 54 may be substantially non-invasively placed near a substantially rigid portion of the anatomy. For example, the dynamic reference frame may include a rhinal dynamic reference frame 100, as illustrated in FIG. 7. The rhinal dynamic reference frame 100 may include a body 102 and an optional tensioning device 104. The rhinal dynamic reference frame 100 is formed to generally fit over a bridge 106 of a nose 108 of the patient 14. Generally, the bridge 106 of the nose 108 is covered with a substantially thin layer of dermal tissue. Therefore, the bridge of the nose 106 is substantially rigid relative to the patient 14. In addition, the tensioning member 104 may be provided to stabilize any portion of the skin that may move relative to the bridge 106 of the nose 108. However, the adhesive portion fixed on the bottom of the dynamic reference frame 100 may simply be the only adhesive necessary to fix the rhinal dynamic reference frame 100 to the bridge 106 of the nose. Nevertheless, the rhinal dynamic reference frame 100 may allow for the dynamic reference 100 to be fixed to the patient 14 in a substantially rigid and repeatable place.

Not only may the rhinal dynamic reference frame 100 be fixed to the bridge 106 of the nose, but the dynamic reference 100 may be substantially molded to a particular portion of the nose 108. Therefore, a molded or moldable inferior portion 110 of the rhinal dynamic reference frame 100 may be fitted to a selected portion of the nose 108. The dynamic reference frame 100 may be positioned and repositioned relative to the bridge 106 of the nose 108 a plurality of times with substantially repeatable placements of the dynamic reference frame 100.

The repeatable substantially precise placement enables the dynamic reference frame 100 to be removed and replaced onto the bridge 106 of the nose 108 without substantially introducing error into the positioning of the dynamic reference frame 100. This allows initial pre-operative images to be taken with the dynamic reference frame 100 in place and used as a fiducial marker. The rhinal dynamic reference frame 100 may then be removed from the patient 14 prior to the operative procedure. Subsequently, during the operative procedure, the rhinal dynamic reference frame 100 may be repositioned on the patient 14. Because the molded portion 110 of the rhinal dynamic reference frame 100 is substantially fitted to a particular portion of the bridge 106 of the nose 108, the rhinal dynamic reference frame 100 can be substantially positioned in the same position as during the pre-operative images. Therefore, the rhinal dynamic reference frame 100 allows for substantially error free referencing of the patient and registration of the patient 14 to the pre-operative images that may be displayed on the display 36. This allows the rhinal dynamic reference frame 100 to be used as both the dynamic reference frame 54 and as a fiducial marker for registering of the pre-operative images.

In addition, it will be understood that the dynamic reference frame 100 may be positioned in any appropriate manner. As illustrated above, the dynamic reference frame 70 may be fixed to a substantially flat portion of the anatomy of the patient 14. Alternatively, the anatomic or rhinal dynamic reference frame 100 may be molded to a substantially uniquely shaped portion of the anatomy of the patient 14. It will be understood that other portions of the anatomy may also be substantially molded to fit a particular portion of the anatomy.

Figure 8:
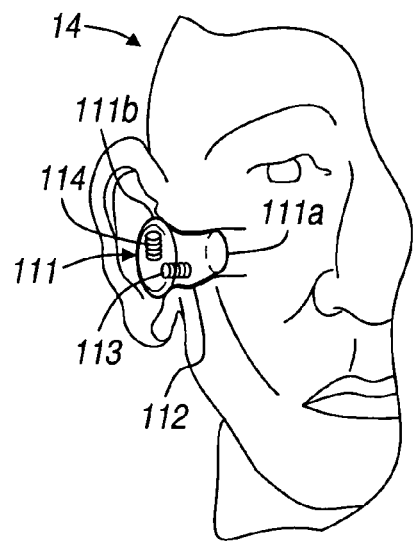
FIG. 8 is an environmental view of another non-invasive dynamic reference frame according to various embodiments

With reference to FIG. 8, a further alternative embodiment of the dynamic reference frame includes an anatomic or inner-cochlear dynamic reference frame 111. The inner cochlear dynamic reference frame 111 is generally molded to fit a portion or the cochlear portion of the ear 112. The cochlear portion of the ear 112 generally includes a substantially unique topography that may be used to fit the dynamic reference frame 111 in substantially only one position. Therefore, as discussed in relationship to the rhinal dynamic reference frame 100 that includes the moldable portion, the inner-cochlear dynamic reference frame 111 may also be formed, at least partially, of a moldable material.

For example, a distal portion 111a of the inter cochlear implant 111 may be formed of a substantially moldable material that may be press fit into the cochlear portion 112 of the ear of the patient 14. After being molded to the cochlear portion 112 of the ear of the patient 14, the moldable material may be cured to substantially maintain the molded shape. An exterior or proximal portion 111B of the inner-cochlear implant 111, may be formed of a moldable or a non-moldable material. Therefore, the inner-cochlear implant 111 may be formed of two materials. Nevertheless the proximal portion 111b, or any appropriate portion, may also include a first sensing coil 113 and a second sensing coil 114. The sensing coils 113, 114 may be positioned in any appropriate manner but may be positioned at angles relative to one another. Therefore, the inner-cochlear implant may provide six degrees of freedom information regarding motion of the inner-cochlear dynamic reference frame 111 during use.

The position of the sensors 113, 114 may be referenced and calibrated after molding of the inner-cochlear implant 111. Therefore, the position of the head of the patient 14 may be known based upon the sensed position of the inner-cochlear dynamic reference frame 111. In addition, as discussed in relation to the other dynamic reference frames, the coils 113, 114 may be passive or active. If the coils 113, 114 are active, the inner-cochlear dynamic reference frame 111 may include a power source, such as battery.

The inner-cochlear dynamic reference frame 111 may also be substantially molded as a separate procedure. For example, such as forming an inner-cochlear hearing aid, the inner-cochlear dynamic reference 111 may be molded to the cochlear portion of the ear of the patient 14 and the inner-cochlear dynamic reference frame 111 may be formed separately after the impression is made. Nevertheless, the molding of the inner-cochlear dynamic reference frame 111 relative to the cochlear portion of the ear 112 with the patient 14, allows for a substantially repeatable placement of the inner-cochlear dynamic reference frame 111 relative to the patient 14. Therefore, images displayed on the display 36 may be substantially easily registered relative to the known location and repeatable location of the inner-cochlear dynamic reference frame 111.

It will be understood that the molded portions may be substantially permanently molded or reusably molded. For example, a curable material may be included, in any appropriate dynamic reference frame, such as the inner-cochlear dynamic reference frame 111. The moldable portion of the cochlear implant 111 may be molded to a portion of the ear or press fit into the ear and then cured to substantially maintain the molded shape. Therefore, the dynamic reference frames may be substantially non-invasively positioned relative to the patient to allow for dynamic referencing of the patient 14 during the operative procedure.

In addition, the dynamic reference frame may be formed almost entirely of the substantially molded material. Therefore, the dynamic reference frame may include a molding material that may be molded to a selected portion of the anatomy and then cured to maintain the shape of the anatomy and also may be formed to include an area to receive the sensor bobbin 90. Although it will be understood that any appropriate coils may be used to form the sensor and may include substantially separate coils that can be positioned into the moldable material substantially separately and removably.

It will also be understood that the dynamic reference frame 54 may be fixed to any appropriate portion of the anatomy. As discussed above, the dynamic reference frame may be positioned relative to the nose 108, the chest of the patient 14, the head of the patient 14, also the dynamic reference frame may be formed as a bite block that may be fitted onto selected portions of the oral anatomy. Also, the dynamic reference frame may be fitted onto or in a tooth cap that may be fit over a tooth, an oral bite block that may be held within the teeth or jaws of the patient or any other appropriate location.

Figure 9:
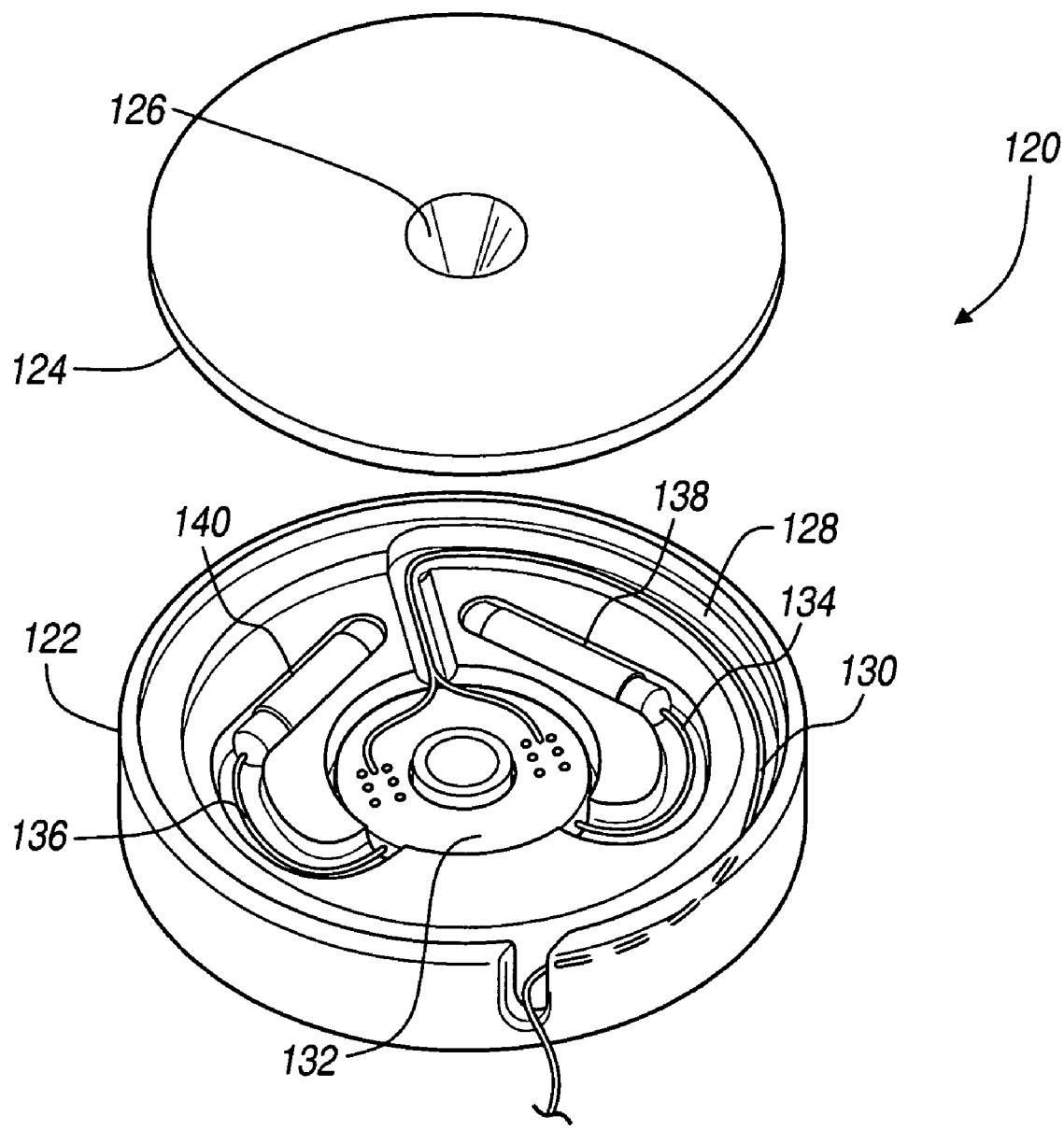
FIG. 9 is an exploded perspective view of another non-invasive dynamic reference frame according to various embodiments.

The dynamic reference frame 54 may either be substantially wireless and powered by an internal power source or may be wired. For example, a hard wire dynamic reference frame 120 is illustrated in FIG. 9. The hard wire dynamic reference frame 120 includes a bottom body portion 122 and a top body portion or cap 124. The cap 124 is generally able to mate with the bottom portion 122 in an appropriate manner and may include a recess 126 to receive the head of a screw to lock the top 124 to the bottom 122. Formed in the bottom portion 122 is a groove 128 that is able to receive a wire such as twisted pair wire 130. The wire 130 may include leads that are soldered to a printed circuit board (PCB) 132. The PCB 132 may include traces that are translated or connected to intermediate wires 134 and 136 that are able to transfer power or a signal to and/or from a first coil 138 and a second coil 140. The coils 138, 140 are generally coils of wire that generate an induced current by an electric field or may transmit an electric field.

The line 130 may operatively interconnect the hard wired dynamic reference frame 120 to the navigation interface 50. Therefore, the hard wire dynamic reference frame 120 may transmit the navigation signals received by the coils through the transmission line 130. Alternatively, as discussed above, an internal power source may be provided such that the information received by the coils 138, 140 may be wirelessly transmitted to the navigation controller 34 using known wireless technology.

The hardwire dynamic reference frame 120 may include any appropriate dimensions. For example the hardwire dynamic reference frame 120 may be about 2 mm to about 10 millimeters in height. Generally, the less the height of the dynamic reference frame the less the possibility for error in transmitting the location of the coils relative to the patient 14. Also, the inferior surface at the base 124 may include a radius to mate with a selected anatomical region, such as a forehead.

The hard wire dynamic reference frame 120 may still be fixed to the dermis of a patient 14 in any appropriate manner. For example, the tensioning member 84 may be provided over the top of the top portion 124 of the hard wire dynamic reference frame 120. In addition, an adhesive may be provided on the inferior portion of the hard wire dynamic reference frame 120.

In addition, the hard wire dynamic reference frame 120, particularly the upper portion 124 and the lower body portion 122, may be formed of an appropriate material. For example, materials may include non-conductive materials such as ceramic or various polymers. In addition, the hard wire dynamic reference frame may be formed of non-conductive carbon fiber materials. In addition, the coils 138, 140 may include conductive carbon fiber materials as the coil component. In addition, the PCB 132 need not be present and the wires may simply be fixed to the coils 138, 140 from the lead 130. Nevertheless, various selections may be chosen to include the PCB 132 or to wire the lead 130 directly to the coils 130, 140.

Therefore, it will be understood that the dynamic reference frame may be formed in any appropriate shape. In addition, the dynamic reference frame 54 may be substantially moldable or non-moldable depending upon the selected shape or position for positioning the dynamic reference frame. Nevertheless, the dynamic reference frame 54 is substantially positioned non-invasively on the patient 14. Therefore, rather than fixing the dynamic reference frame in an invasive manner, such as with bone screws or the like, the dynamic reference frame may be fixed to the patient in a substantially error reducing manner using the tensioning members or a substantially molded portion.

In addition, more than one dynamic reference frame may be provided on the patient 14. More than one dynamic reference frame may be provided for error correction or error detection. Nevertheless, the inclusion of the non-invasive dynamic reference frames may be allowed for substantially simple positioning of the dynamic reference frames during an operative procedure. In addition, the dynamic reference frames 54 may be easily positioned relative to the patient 14 in a substantially quick manner as well. Therefore, the unexpected need for a dynamic reference frame 54 may be solved by simply fixing the dynamic reference frame 54 to the patient 14 using the various constructs. The dynamic reference frame 54 may also be fixed to the patient 14 in any appropriate manner. Such adhesives may be painted on, sprayed on, or include "double-sided" tape. Regardless, the adhesive allows for simple placement of the dynamic reference frame 54 for a selected procedure.

The size, such as the height, the width, etc. of the dynamic reference frame may be selected depending upon selected characteristics. For example, the hard wire dynamic reference frame 120, which may also be substantially wireless dynamic reference frame, may include a select height that is substantially shallow or low to allow for a reduced possibility of movement of the dynamic reference frame 120. In addition, the height or distance of the coils 138, 140 from the anatomy of the patient 14 is small. Therefore, any movement of the hard wire dynamic reference frame 120 is substantially closer to movement of the patient 14 than if the coils were positioned further from the patient 14. Therefore, the size of the dynamic reference frame may also be chosen depending upon the selective amount or error of the system.

In addition, as briefly mentioned above, the coils 138, 140 may be provided in the hard wire dynamic reference 120 or in any appropriate dynamic reference frame. Generally, the coils 138, 140 are substantially similar in functioning to the coils 96 and 98 on the sensor bobbin 90. Simply, the coils are positioned in a slightly different position, but angled relative to one another to provide sensing of six degrees of freedom.

Therefore, whether the coils are substantially positioned on the single member, such as in the sensor bobbin 90, or separated such as the coils 138, 140 in the hard wire dynamic reference 120, still provide the required information for sensing the location of the dynamic reference frame.

Any of the dynamic reference frames (which also may be wireless) may be used as the dynamic reference frame 54, such as the dynamic reference frame 70, the intercochealor dynamic reference frame 111, or the hardwire dynamic reference frame 120 may include various selected characteristics. For example, the sensor portion, such as the included respective coils, may be removable for various reasons. If an imaging technique, such as an MRI is used to image the patient and the dynamic reference frame is left as a fiducial marker, the electromagnetic coils may be removed. Therefore, it will be understood that the coils may either be permanently included within the dynamic reference frame or may be removable therefrom, particularly when the dynamic reference frame is used as a fiducial marker.

In addition, the dynamic reference frame may be used as a fiducial marker. For example, the dynamic reference frame may include a region that is substantially matable or molded to mate with a portion of the anatomy in substantially one way. In addition the dynamic reference frame may also include a portion that is inherently contoured to mate with a portion of the anatomy without including a moldable portion. This allows substantially precise replacement and repeatability of placement of the dynamic reference frame to be achieved.

Because of the precise repeatable placement of the dynamic reference frame it may also serve as a fiducial marker that may be used in preoperative imaging to be a fiducial marker for use during registration intra-operatively. Therefore, the dynamic reference frames may include materials that are substantially radio-opaque or opaque to the imaging process. Various materials may be used to form the radio-opaque dynamic reference frames, such as selected metals, selected compounds, and various mixtures.

Moreover, if the dynamic reference frame is used as a fiducial marker, it may be selected to include portions on the dynamic reference frame that may be viewed on the preacquired image and during the procedure. For example, as discussed in relationship to the dynamic reference frame 70, the dynamic reference frame may include the reference dimple or landmark 80. It will be understood that a plurality of the reference dimples may be provided on the dynamic reference frame 70 for use during an operative procedure to reference the patient space to the image space. The number of reference points, which either may be physical portions, such as the dimples, or markings on the dynamic reference frame, are generally viewable and identifiable on the pre-acquired images, so that each may be matched to a selected portion of the dynamic reference frame during the operative procedure. This allows for multiple degrees of freedom and allows an appropriate and precise registration of the patient space to the image space.

In addition, it will be understood that each of the dynamic reference frames include a portion that allow the dynamic reference frame to be held relative to the patient 14. Therefore, each of the dynamic reference frames includes a selected holding portion. For example, the holding portion may include the adhesive that adheres the dynamic reference frame to a selected portion of the patient 14. In addition, the moldable portion, such as the moldable portion of the intercochealor implant 111a, may be a holding portion and no other portion may be provided to hold the intercochealor dynamic reference frame 111 relative to the patient 14. Regardless, each of the dynamic reference frames may include a holding portion that allows the dynamic reference frame to be held relative to a patient. It may be that the holding portion defines a substantially matable and repeatable placement of the dynamic reference frame relative to the patient 14, such that the dynamic reference frame may also be repeatably precisely placed and may be used for various purposes, such as a fiducial marker.

Figure 10A:
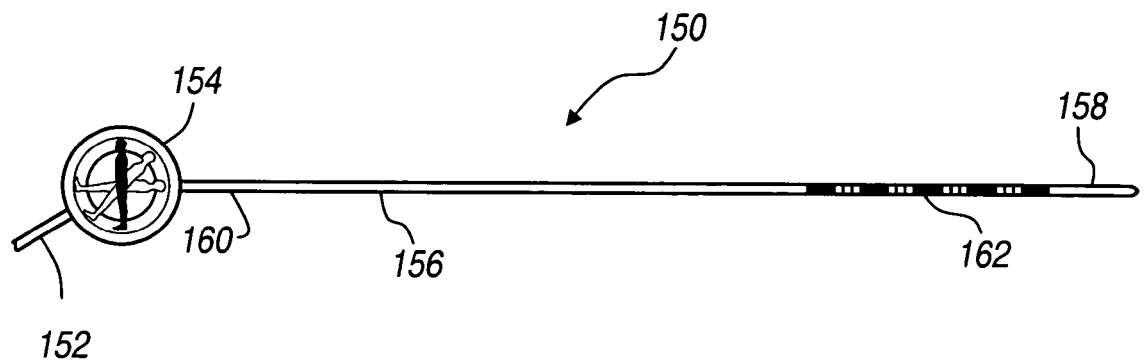
FIG. 10A is a side elevational view of a stylet.
Figure 10B:
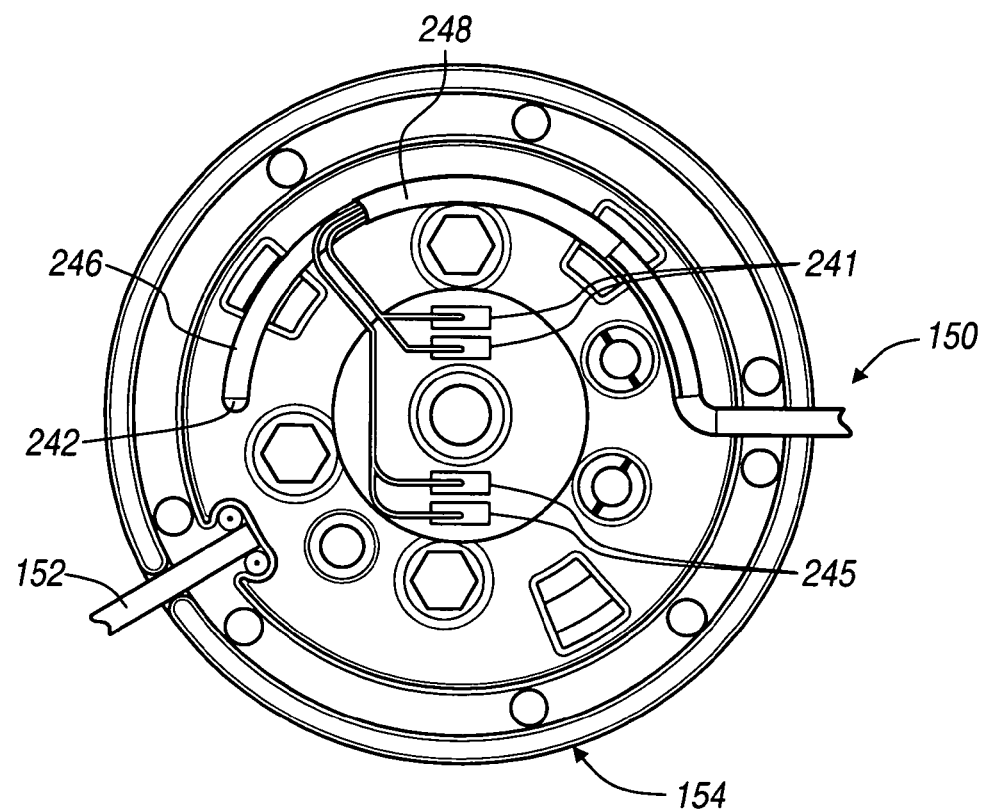
FIG. 10B is a detail interior view of a connection portion of the stylet of FIG. 10A.

Various instruments may be included for use in a selected procedure, such as a stylet 150, with reference to FIGS. 10A and 10B. The stylet 150 generally includes a connection wire or cable 152 and an electronic lead and/or handle 154. Extending from the handle 154 is a stylet portion 156 that is generally moved within the cavity of the patient 14. For example, the stylet 150 may be the instrument 52 rather than the catheter. Therefore, the stylet 150 is an exemplary instrument 52.

Generally, the stylet portion 156 includes a distal or tip end 158 and a proximal end 160. The stylet may be positioned through a cannula and may be used to guide the cannula, though the stylet 150 may be used for any appropriate reason. Positioned near the distal end 158 is a sensor 162. The sensor 162 may be a coil, or multiple coils, to interact with the field transmitted by the transmitter coil array 48. Briefly and described in detail herein, the sensor 162 is generally wrapped around an internal highly electromagnet permeable core insulated with a heat shrink or any appropriate dielectric material. The details of the process and the sensors 162 are described in further detail herein.

With additional reference to FIGS. 10A and 10B, the handle 154 of the stylet 150 may include an area to connect the wires from the coils. A first set of contacts 241 provide an area for contact to each of the leads of the first coil 240. A second pair of contacts 245 is provided for the leads of the second coil 244. In this way, power or sensor leads may be attached to the handle or sensor region 154 for receiving the sensitive information of the sensors or coils 240, 244.

Figure 11:
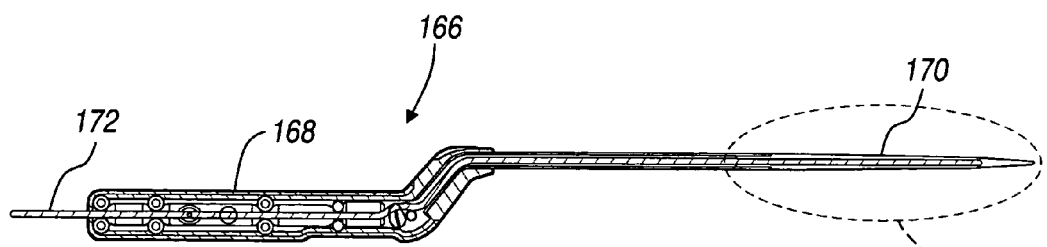
FIG. 11 is a cross-sectional view of a probe including a navigation sensor.

With reference to FIG. 11, a probe 166 is illustrated, as a further alternative for the instrument 52, and generally includes a handle portion 168 and a probe tip 170. The handle 168 is generally formed of a non-metallic material that can be easily grasped and isolated from the electrical lead 172. The electrical lead generally provides a current to a portion of the tip 170.

Figure 12:
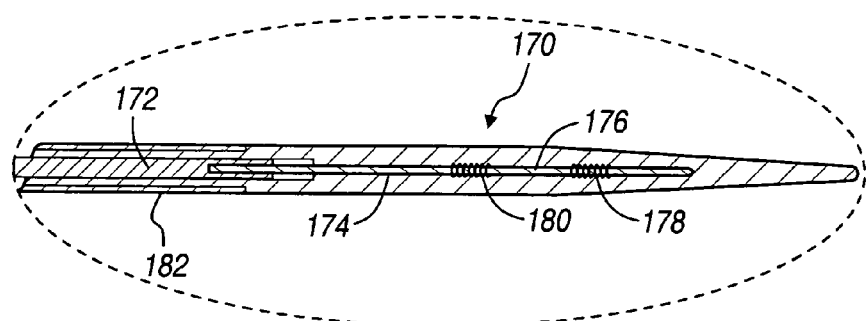
FIG. 12 is an enlarged view of the probe about circle 12 in FIG. 11.

With continuing reference to FIG. 11 and additional reference to FIG. 12, a tip sensor 174 may be positioned in the tip 170 of the probe 166. The tip 170 generally is formed of a non-metallic and/or a non-conductive material. Inside of the tip 170 is a metal shaft 176 that can be formed of an appropriate electromagnetic permeable material. Formed around the metal shaft 176 is a sensor coil 178. A second sensor coil 180 may also be provided. The first and second sensor coils 178, 180 are generally co-axial and formed along the axis of the permeable rod 176. The tip 170 and the rod 176 with the coils 178, 180 are generally positioned within a tube portion 182 of the probe 166. As discussed, the lead 172 provides power to the sensor portion including the coils 178, 180. The sensor portion including the coils 178, 180 may be similar to the sensor portion 162 of the stylet 150 and described in detail herein. Regardless, the sensor portion is generally positioned substantially at the tip or the distal end of the probe 166 to allow for substantially accurate measurement of the position of the tip of the probe.

Figure 13:
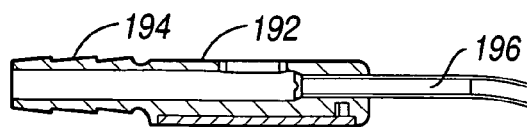
FIG. 13 is a cross-sectional view of a suction instrument according to various embodiments.
Figure 13:
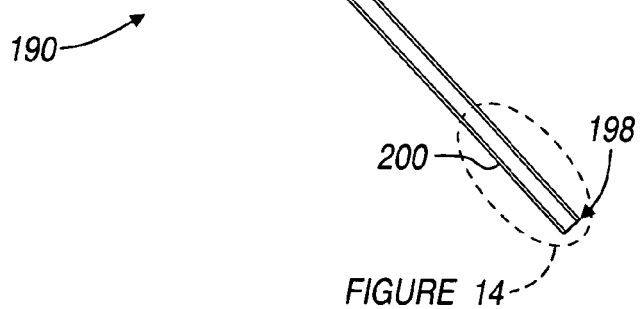
Figure 14:
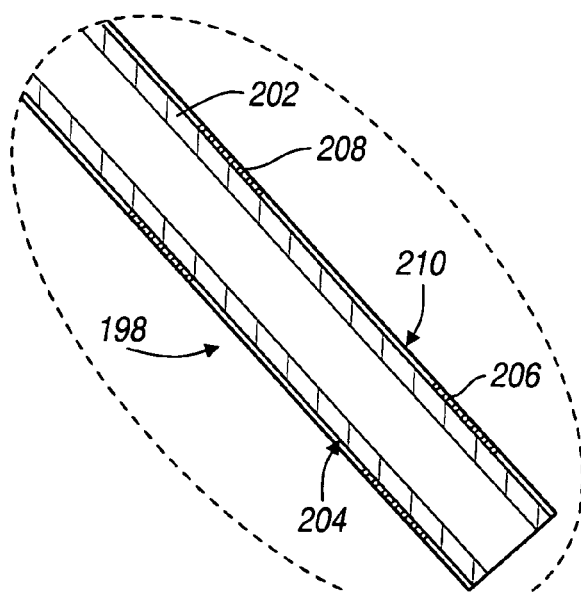
FIG. 14 is an enlarged view about the circle 14 of FIG. 13.

With reference to FIGS. 13 and 14, a suction device 190 is illustrated. Again, the suction device 190 generally includes a handle 192 which includes a connection area 194 to be connected to a suction source. A cannula opening 196 runs the length of the suction portion such that material may be suctioned through a distal tip 198 of the suction instrument 190. Also provided through the handle 192 may be a power source that is able to energize a sensor or sense an electromagnetic field that is acting upon a sensor 200 positioned in the tip 198.

With particular reference to FIG. 14, the suction instrument 190 near the tip 198 generally includes an internal ductile and possibly conductive or nonconductive tube 202. Positioned over the tube is an inner dielectric layer 204. Coils 206 and 208 may also be positioned over the dielectric layer 204. Finally, the sensor 200 may be sealed with an outer dielectric layer 210. Again, the formation of the sensor 200 is described herein including the two coils, 206, 208. Generally, the coils are positioned near the tip 198 of the suction instrument 190 and to provide for substantially accurate position data for the tip 198 of the suction instrument 190. Therefore, the tip 198 of the suction instrument 190 may be moved and the sensor 200 is positioned substantially near the tip 198 so that intended or unintended motion of the tip 198 relative to the handle may be determined.

The sensors, according to any embodiment described above, are generally positioned near a distal end or movable end of an instrument, such as the suction instrument 190, the probe 166, or the stylet 150. Generally, the position of the various instruments, particularly the ends of the instruments, is determined by the known location of a sensor or a transmitting coil and the known size, length, and other physical attribute of the instrument. Therefore, the sensor may be positioned away from or disposed a distance from the extreme end of the instrument. Although a very small and tolerable error may be introduced when the instruments are flexed or move unexpectedly, but this may also cause the exact location of the tip to not be known. This may require many repositioning and attempts to complete a procedure. This error may be detected or substantially eliminated when the sensor is positioned near the distal tip of the instrument, particularly when the instrument is flexible. Therefore, rather than determining or knowing the various physical characteristics of the instrument, the actual sensed portion is the end that may move expectedly or unexpectedly. Therefore, providing the sensor near the distal tip may provide for substantial accurate position data of the instrument.

Generally, the position of the instrument is displayed on the display 36 and is not generally viewable by a user because it is within the cavity of the patient 14. Therefore, the user is generally dependent upon the accuracy of the display 36 to ensure the proper location, orientation and other attributes of the instrument relative to the patient 14. For example, as illustrated in FIG. 1, the instrument 52, such as the catheter, is positioned relative to a specific portion of a heart of the patient 14. Similarly, the stylet 150 may be positioned relative to an extremely particular and precise portion of the brain. Therefore, it may be selected or desirable to substantially eliminate any error when determining the position of the instrument relative to the patient 14.

Although the following description relates generally to the formation of the sensor 162 for the stylet 150, it will be understood that the sensor may be used in any appropriate instrument 52, such as the catheter, the probe 166, the suction instrument 190 or any other appropriate instrument. In addition, the instruments may include any selected tip shape or sizes depending upon a selected use of the instrument. For example, an arthroscope or camera may be provided in the tip for viewing on the display 36 or any other appropriate display. Nevertheless, the sensor may be positioned near the lens portion such that the exact and precise location of the lenses is known.

In addition, various portions of the instrument may be ductile or movable such that the tip is not at a fixed location relative to other portions of the instrument. Therefore, the tip may be movable while the handle is substantially fixed at a known location. Therefore, the sensor positioned at the tip is able to provide the position of the tip even though the handle has not moved.

It will also be understood that various handle calibration and verification points may be included as well as areas for directing wiring within the various instruments and through the handle. It will be understood that these various portions are provided for directing wiring, allowing verification and calibration and are not described in unneeded detail. In addition, the instruments may be substantially disposable or reusable, depending upon the various material specifics being used and the sterilization techniques.

Figure 15:
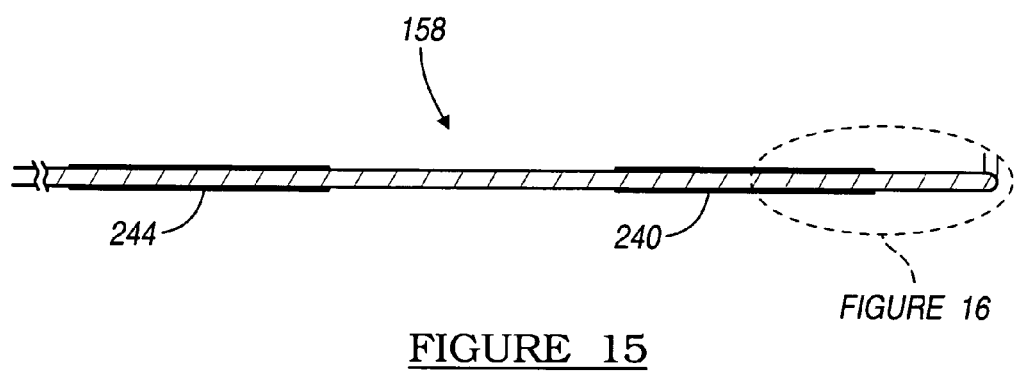
FIG. 15 is a view of a tip of the stylet of FIG. 9A.

According to various embodiments, a method of forming the sensors that can be positioned near the tip in a substantially small volume or space, such as in the stylet tip 158, is described. With reference to FIG. 9 and FIG. 14, the stylet tip 158 is illustrated in detail in FIG. 14. With reference to FIG. 15, a detail of a first sensor coil 240 and an extreme distal tip portion 158A is illustrated. The various coatings or layers around a central rod 242 is illustrated and described herein. Generally, the central rod 242 is a conductive rod and may include various materials such as "302 spring" stainless steel. The material for the rod 242 that is also generally the flexible or steerable portion of the stylet 150 may be any appropriate material. Generally, the material for the rod 242, however, is highly permeable to electromagnetic fields. This generally increases the signal to noise ratio or the gain of the signal of the sent field to a selected amount. Generally, the signal to noise ratio may be increased at least about 5% depending upon the various materials chosen to form the selected construct.

Figure 16:
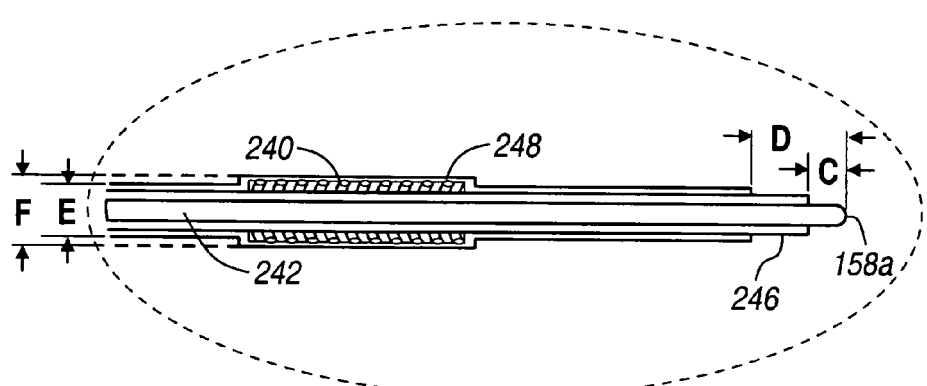
FIG. 16 is a cross-sectional view of the stylet tip of FIG. 15 from circle 16.

With reference to FIGS. 15 and 16 the stylet tip 158 generally includes a first coil and may also include a second coil 244. The first and second coils 240, 244, or any appropriate number of coils may be provided on the tip 158. In addition, the coils 240, 244 may be substantially co-axial or formed at an angle relative to one another. That is, the wire or material used to form the coils 240 and 244 may be wrapped at an angle relative to each other around the rod 242. When the coils are not wrapped at an angle relative to one another, a degree of freedom may not be detected, such as rotation. For various instruments however, such as the uniform stylet tip 158, rotational information may not be necessary and selectively not determined. Nevertheless, for other instruments, such as a suction tube, an ablation tube, or a lens, it may be desired to produce the coils at an angle relative to one another such that rotational direction and location may be determined.

Figure 17:
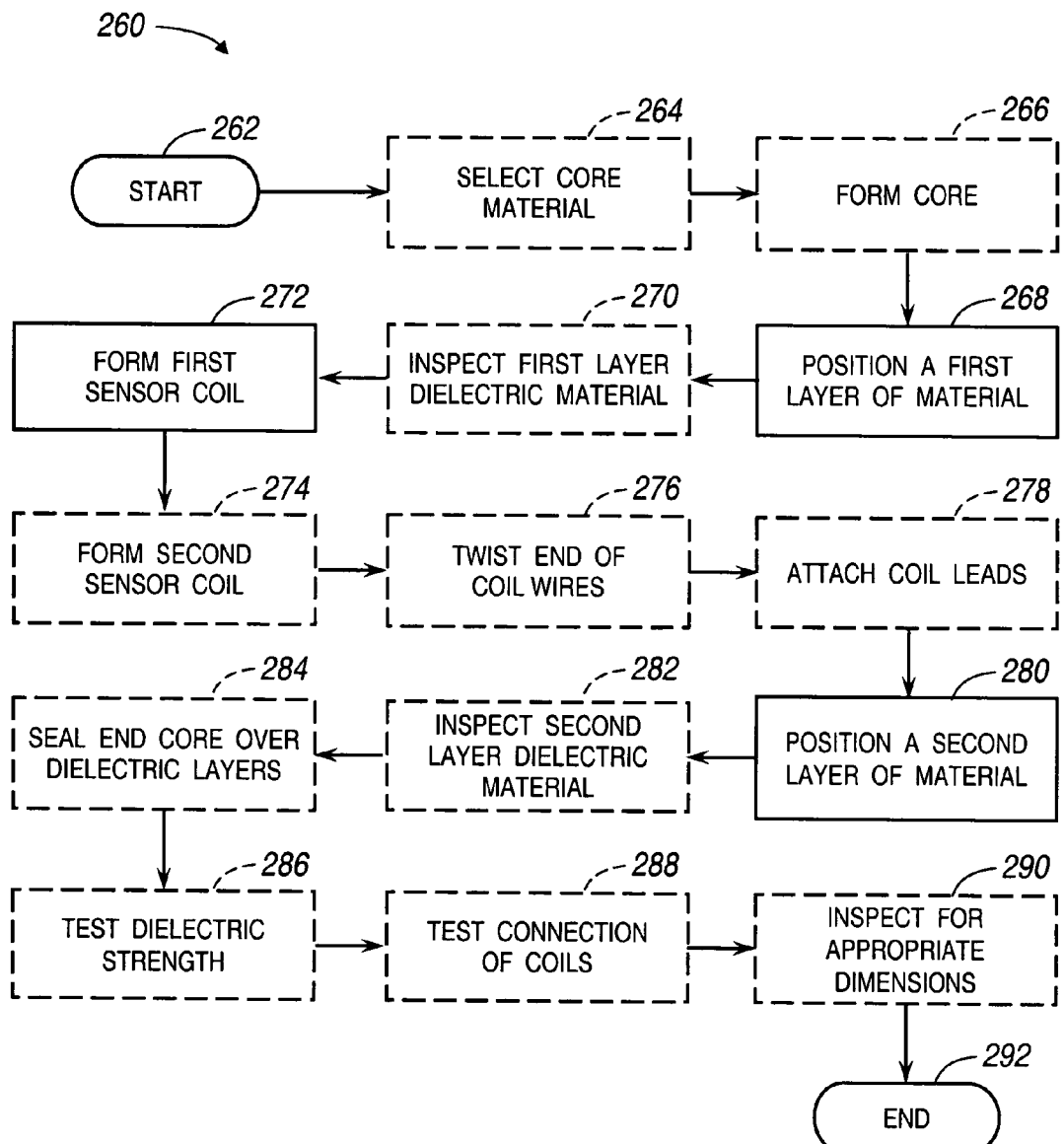
FIG. 17 is a method of forming an electromagnetic sensor according to various embodiments.

As described in detail in flow chart in FIG. 17, prior to forming a coil, a first dielectric barrier or layer 246 may be provided over the rod 242. The first dielectric barrier layer 246 generally is not placed over the extreme end of the tip 158*a* and generally includes a back set or offset distance of about 0.025 mm to about 1.5 mm depending upon the size of the rod 242. For example, the offset distance C may be a selected multiple of a diameter of the rod 242. Not to be limited by the theory, but including the back-set may reduce the possibility of damage to the first dielectric layer 246 during use of the stylet 150. Generally, the extreme tip 159*a* may be used to touch hard surfaces and this may damage the dielectric material. Nevertheless, it will be understood that the first layer of the dielectric material 246 may extend over the extreme tip of the tip 158.

The coils 240, 244 may then wrapped around the first dielectric layer 246. After the coils are positioned over the first dielectric layer 246, a second dielectric layer 248 is provided over the coils 240, 244. Again, the second dielectric layer 248 may be offset a distance D from the extreme end of the tip 158*a*. Nevertheless, it will also be understood that the second dielectric layer 248 may also extend to the end of the tip 158*a*.

It will be understood that the first layer 246 and the second layer 248 need not necessarily be a dielectric material. This is merely exemplary and not intended to limit the scope thereof. For example the material may simply be used to isolate the windings from an exterior environment and the first layer omitted entirely. Alternatively, the wire that forms the coils 240, 244 may be separately or individually coated prior to forming the coils 240, 244. Therefore, the isolation may be achieved without forming a separate layer or coating, such as the first and second layers 246, 248.

Although the apparatus and a very brief process for forming the apparatus is described above, the following description, in addition to the flowchart illustrated in FIG. 17, describes a detailed method of forming the stylet tip including the sensor 162 according to various embodiments. A method of forming a sensor, such as electromagnetic sensor that may be either passive or active, is described in relationship to the flowchart and a method 260. Generally, the method begins a start block 262.

After the process is started in block 262, a material may be selected for form a core in block 264, such as the core 242. As described above, the selected core material in block 264 may be a highly electromagnetic permeable material. Although it is not necessary that the core be highly permeable to electromagnetic fields or be conductive, it may be desirable to provide a highly permeable core for various applications. For example, when forming the stylet tip 158, it may be selected to provide the stylet tip to have diameter no greater than about 1.25 mm. In addition, it may be selected to include a stylet diameter of less than about 1 mm. It may also be desirable to provide a stylet tip 158 in any appropriate diameter or selected property. Therefore, the stylet 158 may be deflectable or bendable according to selected characteristics. Also, at the small diameter the highly permeable material may increase the gain of the field sensed by the coils. Therefore the location information may be more easily determined and sensed.

After the selected core material is chosen in block 264, the core is formed in block 266. The core may be formed according to any selected specifications, such as those described above. Therefore, the core formed in block 266 may include a length, a cross-section, and other various properties that may be selected for the stylet tip 158. Although the material may be selected for the core in block 264 and the core formed in block 266, it will be understood that these steps are optional as steps for forming the selected sensor. The method 260 is exemplary for forming the stylet tip 158. Although the process 260 is exemplary for forming the stylet tip 158, it will be understood that various portions thereof may be used in any process for forming a sensor according to the below described process and a tip sensor in a substantial small area. Therefore, steps that are substantially optional are positioned in blocks that are outlined with dashed or phantom lines and will be indicated as optional herein. Therefore, it will be understood that various steps, although described, are not required to form the sensor as described herein. Therefore, the process is merely exemplary and various specific details are provided only for clarity and not intended to limit the description or the appended claims.

After the core is optionally formed in block 266, a first layer of material is positioned over the core in block 268. The first layer of material positioned in block 268 may be a dielectric. Though the material for the first layer may be any appropriate material and is merely exemplary a dielectric. The first layer of the dielectric material may be positioned over the core in any appropriate manner. For example, the first layer of the dielectric material may be positioned over the core as a heat shrink or shrink wrap process. This being that a portion of the material may be formed as tube and slide over the core and then shrunk to substantially engage the core along its length. Alternatively, the material may be painted on or sprayed on the core formed in block 266.

For any or all of these processes, a plurality of layers of the material may be positioned on the core to form the first dielectric layer of a selected thickness. The thickness of the dielectric layer may be any appropriate thickness according to selected characteristics. For example, the thickness of the first layer of the dielectric material may be about 0.00025 inches to about 0.03 inches (about 0.00635 mm to about 0.762 mm). Generally, however, the first layer of the dielectric material may be about 0.001 inches (about 0.0254 mm) in thickness.

The dielectric material may also be any appropriate dielectric material to achieve selected results. For example, it may be selected to have dielectric breakdown strength of about at least about 4,000 volts per about 0.001 inches (mil) (about 0.0254 mm) in thickness. Although any appropriate dielectric break down strength may be selected. Also, it may be selected to choose other properties for the first dielectric layer placed in block 268. Various materials may be used such as polyester shrink tubing or ULTRATHIN WALL POLYESTER (PET) shrink tubing provided by Advanced Polymers Inc. of Salem, N.H. Although any appropriate material may be used, it may be selected to include the dielectric breakdown strength of at least about 1000 volts per mil.

After the first layer of dielectric material is positioned on the core, the layer may be inspected in block 270. The inspection may be any appropriate inspection such as a visual inspection, magnification inspection, or various electrical tests to ensure that the selected installation is achieved. Also, the first layer of dielectric material may be inspected to ensure that it has been positioned on the core in a selected manner. As described above, it may be selected to only cover a selected portion of the core and not extend the first layer of dielectric material substantially to the tip of the core. As illustrated in FIG. 15, it may be selected to position the first layer of dielectric material 246, the distance C from the extreme end 158*a* of the tip 158.

After the optional inspection of block 270, a first sensor coil is formed in block 272. The sensor coil, such as the coil 240 illustrated in FIG. 15, may be formed using any appropriate materials. For example, a 48 gauge magnetic wire that is coated with a single built polyurethane with butyl bonds may be wrapped around the core including the first layer of dielectric material to form the first sensor coil.

The wire may be wrapped around the first layer of the dielectric material in any appropriate manner. For example, the coils may be wrapped substantially co-axially with a longitudinal axis of the core. Alternatively, the wire may be wrapped substantially at an angle to the core for selected reason, such as sensing rotation of the core during use. As an example, a first sensor coil may include a first layer of coils including approximating 300 turns and a second layer positioned over top of the first layer also having approximately 300 turns. Therefore, the first coil formed in block 272 may include approximately 600 turns. Nevertheless, it will be understood that only a single layer or any number of layers may be used and that any appropriate number of turns may be used to form the first sensor coil in block 272.

The first coil formed in block 272 is exemplary wound around the first layer positioned in block 268. It will be understood that the wire used to form the coil in block 272 may first be coated or may be a coated wire. When the wire is coated or covered positioning the first layer of material in block 268 may be omitted. The coating on the wire may provide all of the properties, such as electrical, environmental and the like, that the material in the first layer formed in block 268 may otherwise provide.

An optional second coil, which may also be formed of coated or covered wire, may be formed in block 274. Therefore, it will be understood that any appropriate number of coils may be formed for reasons discussed herein but may include a first coil formed in block 272 and a second coil formed in block 274. If there are two coils, the second coil may be positioned a selected distance from the first coil. For example, the first coil may have an edge that is about 0.25 mm to about 10 mm from an end of the second coil. Nevertheless, it will be understood that the coils may be positioned at any appropriate position on the tip 158 and relative to one another.

After the first sensor coil is formed in block 272 and optionally the second sensor coil in block 274, the ends of the wires forming the sensor coils may optionally be twisted in block 276. The ends of the wires that form the coils formed in blocks 272 and optionally in block 274 may be twisted in any appropriate manner. For example, the wires may be twisted in about 10 to about 30 twist per inch and may be uniformly twisted rather than twisting one around the other. Although it will be understood that the wires may be formed in any appropriate manner and that twisting the wires in block 276 is merely optional.

After the wires are optionally twisted in block 276, the ends of the coils are attached to locations on the stylet handle in block 278. Generally, the leads of the coil are attached to selected positions, such as to a printed circuit board or to other wire leads, that allow for interconnection to various components, such as the navigation interface 50 (FIG. 1). The coil leads that are attached from block 278 may be attached to any appropriate portion and may be from either the first sensor coil formed in block 272 or the optional second sensor coil formed in block 278.

After the leads from the coils are attached in block 278, or at any appropriate time, a second layer of material may be positioned in block 280. The second layer of material positioned in block 280 may be any appropriate material and is only exemplary a dielectric. The second layer of dielectric material may be positioned over both of the first layer of dielectric material, that was positioned in block 268, and over the sensor coil formed in block 272, and optionally in block 274. The material that is used to form the second layer of the dielectric material may be the same or different than the material chosen to form the first layer of the dielectric material in block 268. In addition, the method of positioning the second layer of the dielectric material in block 280 may also be the same or different that the method used to position the first layer of dielectric material in block 268. For example, the first layer of the dielectric material positioned in block 268 may be a substantially heat shrink or shrink tubing that is positioned over the core formed in block 266 and then shrunk according to any selected method, such as heating. Alternatively, the second layer of dielectric material positioned in block 280 may be sprayed or painted on over. In addition, the material may be the same, such as the Ultra Thin Wall polyester (PET) heat shrink tubing produced by Advanced Polymers Incorporated or may be any other appropriate material.

Nevertheless, the second layer of the dielectric material may include the same or different dielectric break down strength in the first layer. For example, the dielectric breakdown strength of the second layer of the dielectric material may be at least 4000 volts per mil or may be any other appropriate amount.

Briefly, as an example, the first layer of the dielectric material may provide insulation between the sensor coil formed in block 272 and the core formed in block 266. Therefore, the sensor coil formed in block 272 is electrically isolated from the core formed in 266. This allows the core formed in 266 to also be a conductive material and may also act as a core and a gain amplifier for the sensor coil, as described further herein. In addition, the second layer of the dielectric material may act as an electrical insulator relative to a patient or a portion exterior to the core and as an environmental seal to the sensors formed in block 272 and optionally in block 274.

It will also be understood that the second layer of the material positioned in block 280 may also be omitted. It may be omitted for any reason, such as the wires that form the coil formed in block 272 are previously coated. Therefore, the second layer of material formed in block 280 may be omitted. Regardless, the second layer of material may be any appropriate material and need not be a dielectric. The second layer of material in block 280 may be positioned for any appropriate reason, such as a liquid seal, an electrical isolation, etc.

After positioning the second layer of the dielectric material in block 280 the second layer of dielectric material may be optionally inspected in block 282. As in block 270, the material may be inspected according to any appropriate method, such as visual inspection, magnification inspection, and electrical testing.

After the second layer of the dielectric material is optionally inspected in block 282 the ends over the core may be sealed. As illustrated in FIG. 16, the first layer of dielectric material 246 and the second layer of dielectric material 248 may not extend over the extreme tip 158*a* of the core 242. Therefore, it may be selected to seal the extreme end 158*a* over the dielectric layers 246, 248 to achieve a substantially water tight or other material tight seal.

The seal formed optionally in block 284 may be formed in any appropriate manner. For example, the extreme tip 158*a* and any selected length along the tip 158 may be dipped into a selected material, such as Loctite 4014 produced by Henkel Loctite Corp. of Rocky Hill, Conn. The material may substantially seal the interior so that no fluid can be wicked or drawn towards the coil 240 through capillary action. Therefore, the coating of the dielectric layers, blocks 268 and 280 may be sealed in any appropriate manner to ensure that no fluid is allowed to destroy or short the coils formed on the tip 158.

In addition to the steps described above, various other steps such as testing the dielectric strength in block 286, testing the connection of the coil after attaching the coil leads in 278, testing the coils in block 288, and inspecting the construct for achieving the appropriate dimensions in block 290 may be performed. Then the process ends in block 292.

Although various optional steps may have been performed in the method 260 it will be understood that the sensors generally formed by positioning on a first layer over dielectric material over a core, forming a sensor coil around the first layer of the dielectric material in block 272, and positioning a second layer of dielectric material in block 280 over the coil may be performed. In addition, the dielectric materials may be any appropriate materials and are generally provided only for safety considerations. Therefore, simply forming the coil around the core may be performed for any appropriate purpose. Providing the dielectric layers are able to protect the user and the patient from any possible surges and insure that the instrument is not corrupted by environmental degradation.

Furthermore, additional assembly steps may be performed depending upon the selected instrument. As illustrated in FIG. 10, the cable 152 may be interconnected with the connection area 154 and interconnected with the navigation probe interface 50. Alternatively, if the other instruments, such as the probe 166 or the suction tube 190 are formed, the relative handles may be provided and affixed thereto and various other connections may also be performed. Nevertheless, it will be understood that these steps are not necessary for forming the sensor near the tip of the construct.

With reference to FIG. 16 the exterior dimension or diameter E of the tip 158 and of the stylet portion 156 of the stylet 150 may be any appropriate dimension and may be about 0.09 mm to about 1.5 mm in diameter. It will be understood that the dimension may be any appropriate exterior dimension as the stylet portion 160 may be formed in any shape, but may be a cylinder. The diameter E generally includes the dimension of the core 242 the first dielectric layer 246 and the second dielectric layer 248. In addition, a diameter F that includes the diameter or size of the coil 240 may be about 0.9 mm to about 1.50 mm in diameter. Therefore, the diameter F may be greater than the diameter E depending upon whether the space between the coils is selected to be equal to the size as around the coils 240.

Regardless of the actual size, it is desired to include a diameter of the stylet portion 156 that is substantially small for use in various purposes. For example, the stylet portion 156 may generally be provided with a cannula that is positioned in various portions of the anatomy, such as the brain. Therefore, it may be desirable to provide the stylet portion 156 and a plurality of other instruments through the cannula without moving the cannula. Therefore, the stylet may be of a selected diameter that will substantially freely move within the cannula.

Although it may be selected to keep the maximum diameter F under a selected size, it will be understood that any appropriate or selected size of diameter may be used. Simply having a substantially small diameter may provide various selected properties, as having it selected for various instruments and purposes. Again, as described above, various portions of the instrument and the method may be optional and not necessary. Although the core 242 may be formed of a substantially conductive material that is surrounded by the first layer of dielectric material 246, that is able to isolate the coil 240 from the conductive material of the core 242, and the second layer of dielectric material 248 provided to enclose the coil 240 from an exterior environment; it will be understood that various other portions, such as providing the core 242 as the core 176 in the probe 166 or the metal tube 202 on the suction instrument 190 may also be provided.

The core 242 may be formed of any appropriate material, but may be formed of the permeable material that may include ferrous materials such as ferrites like those provided by Fair-Rite Products Corp. of Wallkill, N.Y. The permeable material may provide a gain to the signal of the coils, such as the first coil 240 and the second coil 244 in the stylet 150. The material may provide a gain that is relative to its permeability, especially above the permeability of air. Therefore, the gain experienced may be dependant upon the type of material chosen for the core 242, or any core about which the coils are formed in various embodiments.

In addition, it will be understood that any appropriate number of coils may be provided. For example, the stylet 150 may include the first coil 240 and the second coil 244. As described above, the windings of the coils 240, 244 may be substantially co-axial so that only five degrees of freedom are determined. Nevertheless, the windings of the coils may also be formed at an angle relative to one another so that rotational orientation of the stylet 150 may also be determined. In addition, any appropriate number of coils may be provided along the length of the instrument for various purposes.

For example, two coils that are coaxial may be provided for error detection. The first coil may be provided at a known distance from a second coil. Therefore, the sensed position of the first coil 240 relative to the second coil 244 may be used to detect errors between the positions of the two to determine the exact location of the tip 158 of the stylet 150. In addition, a compensation circuit may be provided to compensate for the sensed signal from the first coil 240 relative to the second coil 244. Therefore, providing two coils in the stylet 150 may be provided for any number of reasons or for all appropriate reasons. In addition, it will be understood that the number and types of coils may be provided in each of the instruments described above and any other appropriate instrument. Nevertheless, a substantially small or narrow sensor coil may be provided according to the steps described above and may also be provided according to the various optional steps described above.

Figure 18:
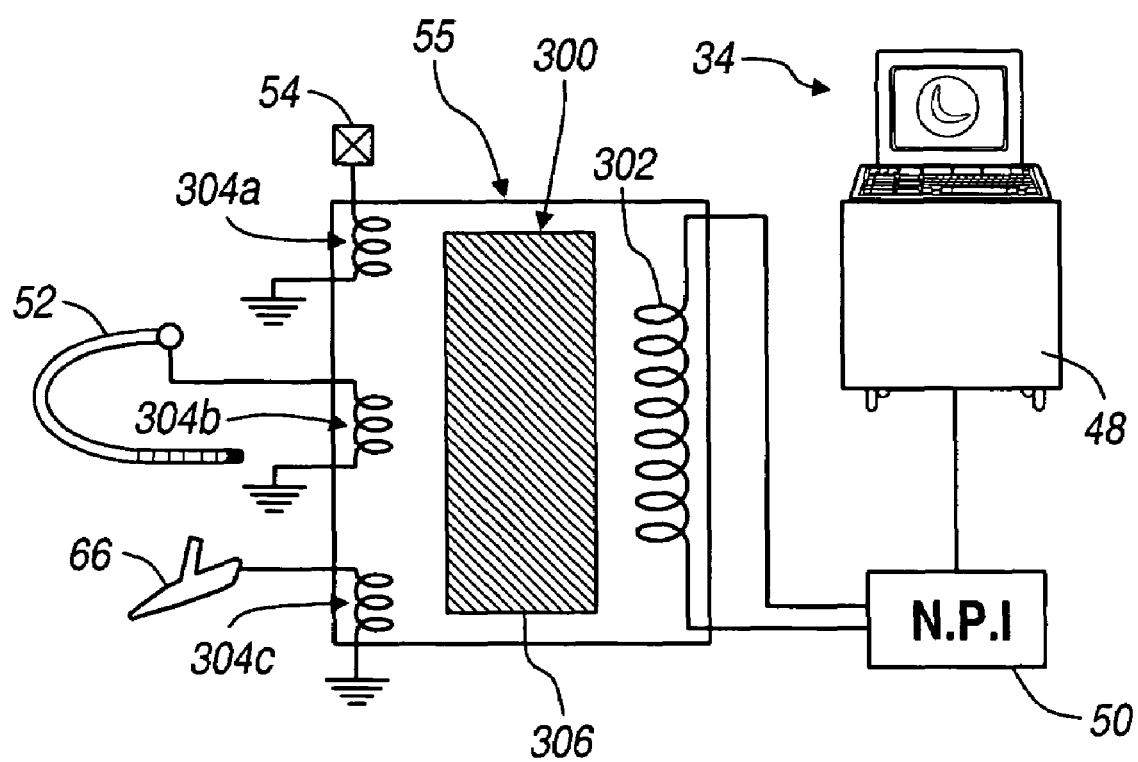
FIG. 18 is a schematic view of an isolator circuit according to various embodiments.

With reference to FIGS. 1 and 18 the isolator circuit 55 may be provided to isolate any portion of the instrument 52 that may engage the patient 14 from the electrical source, such as the work station 34. As illustrated in FIG. 1, the instrument 52, which may include the stylet 150, the probe 166, the suction instrument 190, and/or any other appropriate instrument, is inserted into the patient 14. Each of the instruments may include the sensor 58, as disclosed herein and above, to which an electrical current has provided. In addition, the dynamic reference frame 54, according to any of the embodiments or various other embodiments, as described herein or understood to be included within the scope of the present disclosure, may also includes an electrical lead from the navigation probe interface 50. In addition, any other systems such as the probe 66 may each have an electrical current provided thereto. The isolator circuit 55 may be positioned anywhere to isolate any of these instruments from the electrical source.

The isolator circuit 55 may include any appropriate isolation transformer 300. The transformer 300 may include a first coil 302 that is operable to transmit or receive a signal. The first coil 302 may generally be on an output side that receives a signal and transmits it through the navigation probe interface 50 and to the workstation 34 or the coil array controller 48.

The first coil 302 may be separated from a plurality of second coils 304a, 304b, and 304c by a dielectric or appropriate medium 306. As described herein each of the coils 304a-304c may be in-line with a selected instrument or device. It will be understood, however, that a single second coil may be provided with a plurality of taps connected thereto. The dielectric medium 306 eliminates a current that may attempt to transfer from the first coil 302 to the second coils 304a, 304b, and 304c or vice versa. Nevertheless, an electromotive force may be provided into either of the first coil 302 or the second coils 304a, 304b, and 304c that may couple across the dielectric material 306. In this way, the second coils 304a, 304b, and 304c is electrically isolated from the first coil 302, such that only a potential is able to transfer across the dielectric medium 306.

The second coil 304 may include leads to the dynamic reference frame 54, the instrument 52, such as a catheter, and the probe 66. As discussed above the instrument 52 may also be the stylet 150, the probe 166, and/or the suction tube 190, or any appropriate instrument. Both the first coil 302 and the second coils 304a, 304b, and 304c may also include a ground lead. Generally, the first coil 302 is operably connected to the work station 34 through the navigation probe interface 50. The navigation probe interface may include appropriate power sources and amplifiers as necessary. Therefore, the navigation probe interface 50 may be electronically isolated from the various portions of the assembly 10 that may engage the patient 14. In this way, a current may not be transferred through the electrical isolator 55 to any of the instruments, sensors, or portions that touch the patient, such as the instrument 52 and the dynamic reference frame 54.

In addition, as discussed briefly below, the first coil 302 may include a different number of windings than the second coils 304a, 304b, and 304c. For example, if it is desired to include a stronger signal going back to the navigation probe interface 50, a number of windings in the first coil 302 may be greater than the number in the second coil 304. Therefore, the electrical isolator 55 may also act as an amplification circuit for receiving a signal from the various components, such as the dynamic reference frame 54 and the instrument 52.

As illustrated in FIG. 1, the isolator circuit 55 may be provided on any of the lines from the navigation probe interface 50. Therefore, any electrical surge may be immediately stopped before engaging the patient 14 or instrument 52. Thus, the isolator circuit 55 may be positioned on each of the lines leading to each of the instruments, the probe 66 or the dynamic reference frame 54. Furthermore, the isolator circuit 55 may be incorporated into the navigation probe interface 50 or into any of the instruments 52, the dynamic reference frame 54, or the probe 66. The isolator circuit 55 may be positioned anywhere to eliminate the current that may be unintentionally provided to the patient 14.

For example, with reference to FIG. 9B, the isolator circuit may be included within the circuit capsule 154 of the stylet 150. Therefore, the power provided to the stylet 150 may be interrupted when a selected voltage or current is reached. The isolator circuit may allow stopping a voltage before it is able to pass through the circuit to reach the sensors. The isolator circuit 55 in addition to the dielectric layers positioned over the coils 240, 244, may assist in protecting the patient 14 from undesired electrical shock. In addition, the isolator circuit 55 may be incorporated into any other appropriate portion of the other instruments with a dynamic reference frame.

In addition to isolating the patient 14 from undesired electrical current or shock, the isolator circuit 55 may also act as an amplifier to increase the signal to noise ratio. For example, the isolator circuit 55 may be a step up transformer that is designed to increase the signal to noise ratio a selected amount. For example, a selected side, such as the signal output side, of the circuit may include a number of windings that is greater than the signal input side such that the signal is stepped up and the signal to noise ratio is increased. Therefore, the isolator circuit 55 may not only electrically isolate the patient 14 from an undesirable surge, but may also increase the signal to noise ratio to increase the efficiency of the navigation system 10.

Therefore, the navigation system 10 may be provided to include a dynamic reference frame 54 that is substantially non-invasive such that the patient 14 does not endure further trauma than required from the operative procedure. Generally, the navigation system 10 is able to provide a less invasive or minimally invasive procedure to achieve less trauma to the patient 14. Therefore, providing a substantially non-invasive dynamic reference frame may assist in decreasing the overall trauma or invasiveness of the procedure.

In addition, the sensor coils may further reduce the size of the instrument for various purposes. In addition, the size of the coils may allow the coils to be positioned near the distal end of the instrument to more precisely determine the position of the instrument. Therefore, the position determination of the instrument can be more accurate. For example positional accuracy can be increased by at least about 5% over placing the sensors away from the tip. The procedure may then be performed with fewer attempts thereby again further reducing the possible trauma of the procedure.

Also, the isolator circuit 55 may increase the signal to noise ratio to better determine the position of the various sensors and therefore determine the position of the instrument. In addition, the isolator circuit 55 may assist in isolating the patient 14 from any electrical sources of the navigation system 10. Therefore, the navigation system 10 may increase the efficacy.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. In a surgical navigation system a substantially minimally invasive dynamic reference frame for dynamically referencing portions of an anatomy, comprising:
    a body portion selectively attachable to a portion of the anatomy, the body portion having a sidewall defining an exterior perimeter defining an interior portion and a passage through the sidewall into the interior portion;
    a navigation portion to at least one of sense, transmit, or combinations thereof a characteristic operable to pass through the passage defined by the sidewall and be positioned in the interior portion; and
    a holding section to hold said body portion relative to the portion of the anatomy;
    wherein said holding section substantially non-invasively holds said body portion relative to the portion of the anatomy;
    wherein the navigation portion is operable to be selectively positioned in the interior portion through the passage through the sidewall.

2. The surgical navigation system of claim 1, wherein said characteristic includes at least one of an optical characteristic, a electro-magnetic characteristic, an acoustic characteristic, a light characteristic, and combinations thereof.

3. The surgical navigation system of claim 1, wherein said navigation portion includes at least one coil to at least one of transmit and receive an electro-magnetic field.

4. The surgical navigation system of claim 3, further comprising at least two coils positioned at an angle relative to one another;
wherein a plurality of degrees of freedom of movement of the navigation portion can be determined.

5. The surgical navigation system of claim 1, wherein said holding section includes a tensioning member extending from said body portion to engage at least one of the portion of the anatomy or an area adjacent to a portion of the anatomy.

6. The surgical navigation system of claim 1, further comprising:
a fiducial marker portion.

7. In a surgical navigation system a substantially minimally invasive dynamic reference frame for dynamically referencing a portion of an anatomy, comprising:
a body portion selectively attachable to the portion of the anatomy;
a navigation portion associated with the body portion to at least one of sense a characteristic, transmit a characteristic, or combinations thereof;
a holding section operable to contact an exterior of the portion of the anatomy to assist in holding the body portion relative to the portion of the anatomy;
a fiducial portion operable to be imaged and determined in the image data;
wherein the body portion defines a volume enclosed by an outer surface and a recess within the outer surface of the body portion;
wherein the body portion defines a concave area operable to engage at least a portion of a tensioning member to assist in holding the body portion relative to the portion of the anatomy; wherein said body portion further defines a recess within the volume to receive the navigation portion; wherein the navigation portion is operable to be selectively positioned in the recess through a passage through the outside surface; wherein the navigation portion is operable to be removed from the recess during imaging of the anatomy to assist in eliminating any distortion that may be caused by the navigation portion.

8. The surgical navigation system of claim 7, wherein the navigation portion includes a coil of a conducting material;
wherein said characteristic is an electromagnetic field.

9. The surgical navigation system of claim 7, wherein the recess includes an elongated bore extending from a side of the body portion.

10. The surgical navigation system of claim 7, wherein said body portion and said holding section are formed of a single member.

11. The surgical navigation system of claim 10, wherein said single member is seamlessly and uniformly formed.

12. The surgical navigation system of claim 7, further comprising:
a tensioning member operable to interact with the holding section to assist in holding the body portion relative to the portion of the anatomy.

13. The surgical navigation system of claim 7, wherein at least one of the body portion, the holding section, or combinations thereof define a localization divot.

14. The surgical navigation system of claim 7, wherein at least one of the body portion, the holding section, or combinations thereof define a recess having a surface positioned within the at least one of the body portion, the holding section, or combinations thereof.

15. In a surgical navigation system having a substantially minimally invasive dynamic reference frame for dynamically referencing a portion of an anatomy, the surgical navigation system comprising:
a first section defining a volume sized and operable to be positioned relative to the portion of the anatomy;
a tracking device associated with the first section to at least one of sense a characteristic, transmit a characteristic, or combinations thereof; and
a holding section associated with the first section and operable to assist in holding the first section relative to the portion of the anatomy;
wherein at least one of the first section, the holding section, or combinations thereof defines a recess that is complementary in shape to the tracking device and is operable to receive the tracking device substantially within the volume.

16. The surgical navigation system of claim 15, wherein the first section and the holding section are formed as a seamless uniform member.

17. The surgical navigation system of claim 15, wherein the holding section is sized and configured to substantially match a contour of the anatomy.

18. The surgical navigation system of claim 15, wherein the holding section includes a concave region bound on at least two sides by a first region and a second region where the first region and the second region are substantially planar with one another.

19. In a surgical navigation system having a substantially minimally invasive dynamic reference frame for dynamically referencing a portion of an anatomy, the surgical navigation system comprising:
a first section defining a volume sized and operable to be positioned relative to the portion of the anatomy;
a tracking device associated with the first section to at least one of sense a characteristic, transmit a characteristic, or combinations thereof;
a holding section associated with the first section and operable to assist in holding the first section relative to the portion of the anatomy; and
a tensioning member;
wherein the tensioning member extends over and engages at least a portion of the concave regions defined by the holding section to assist in holding the first section relative to the anatomy.

20. The surgical navigation system of claim 15, further comprising:
a fiducial portion.

21. The surgical navigation system of claim 15, further comprising:
a localization depression;
wherein the localization depression is defined by at least one of the first section, the holding section, or combinations thereof;
wherein the localization depression is operable to interact with a tool.

22. The surgical navigation system of claim 1, wherein said body portion includes an adhesive receiving section;
wherein said adhesive receiving section allows for the placement of the adhesive between said body portion and the anatomy to assist in fixing the body portion to the portion of the anatomy.

23. The surgical navigation system of claim 1, wherein said holding section defines a central trough area that is substantially concave having a first peak on a first side of the body portion and a second peak on a second side of the body portion substantially opposed to each other and a tensioning member extending from said body portion to engage at least one of the portion of the anatomy or an area adjacent to a portion of the anatomy.

24. The surgical navigation system of claim 23, wherein said body portion is substantially cylindrical and the holding section is defined on a first side and an anatomy contacting portion is defined on a second side;
    said anatomy contacting portion defining a depression operable to receive a material;
    a navigation bore defined through a sidewall of the body portion from the passage between the first side and the second side; and
    a localization divot defined at the side wall at a position spaced apart from the navigation portion bore.

25. The surgical navigation system of claim 1, wherein the navigation portion is operable to be removed from the interior portion during imaging of the anatomy to assist in eliminating any distortion that may be caused by the navigation portion.

26. The surgical navigation system of claim 5, wherein the body portion defines a concave area operable to engage at least a portion of the tensioning member to assist in holding the body portion relative to the portion of the anatomy.

\* \* \* \* \*